(12) United States Patent  (10) Patent No.: US 7,803,815 B2
Bissantz et al.  (45) Date of Patent: Sep. 28, 2010

(54) INDOL-3-YL-CORBONYL-PIPERIDIN-BENZOIMIDAZOL DERIVATIVES

(75) Inventors: Caterina Bissantz, Village Neuf (FR); Christophe Grundschober, Rodersdorf (CH); Hasane Ratni, Habsheim (FR); Mark Rogers-Evans, Binningen (CH); Patrick Schnider, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 895 days.

(21) Appl. No.: 11/490,305

(22) Filed: Jul. 20, 2006

(65) Prior Publication Data

US 2007/0021463 A1  Jan. 25, 2007

(30) Foreign Application Priority Data

Jul. 21, 2005 (EP) .................. 05106695
Nov. 9, 2005 (EP) .................. 05110506

(51) Int. Cl.
*A61K 31/454* (2006.01)
*C07D 403/14* (2006.01)

(52) U.S. Cl. ..................... 514/322; 546/199
(58) Field of Classification Search ................ 514/322; 546/199
See application file for complete search history.

(56) References Cited

U.S. PATENT DOCUMENTS 5,686,624 A 11/1997 Di Malta et al.
6,933,316 B2 8/2005 Hsieh et al.

OTHER PUBLICATIONS

Castro et al. "preparation of phenyl indole . . . ." CA130:237469 (1999).*
Sheppard et al. "Indolyl-3-carbonyl . . . ." CA 125::328713 (1996).*
Bissantz et al. "preparation of indole-3-carbonyl . . . ." CA 146:184470(2007).*
Bissantz et al. "Preparation of indol-2-yl-carbonyl . . . ." CA 149:53995 (2008).*
Frohn et al. "New chemical probes . . . ." CA 148:92223 (2007).*
Ebner et al., (2002), Eur. J. Neurosci. vol. 15(2) pp. 384-388.
Liebsch et al., (1995), Regul. Pept. vol. 59(2) pp. 229-239.
Michelini et al., (1999), Ann NY Acad. Sci. vol. 897 pp. 198-211.
Van Kerckhoven et al., (2002) Eur. J. Pharmacol. vol. 449 (1-2) pp. 135-141.
Swain et al., J. Med. Chem. (1991), vol. 34 p. 140-151.
Delgado et al., J. Org. Chem. (1993), vol. 53 p. 2862-2866.
Hagiwara et al., J. Med. Chem. (1994), vol. 37, p. 2090-2099.
Hopkins et al., Bioorganic & Medicinal Chem. Letters (2005) vol. 15(11) pp. 2734-2737.
Sohda et al., Journal of Medicinal Chem. (1992) vol. 35(14) pp. 2617-2626.
Serradeil-Le Gal, C., et al., Progress in Brain Research, vol. 139, pp. 197-210 (2002) XP001205440.

* cited by examiner

*Primary Examiner*—Celia Chang
(74) *Attorney, Agent, or Firm*—George W. Johnston; Patricia S. Rocha-Tramaloni; Kimberly J. Prior

(57) ABSTRACT

The present invention relates to Indol-3-yl-carbonyl-piperidin-benzoimidazol derivatives which act as V1a receptor antagonists and which are represented by Formula I:

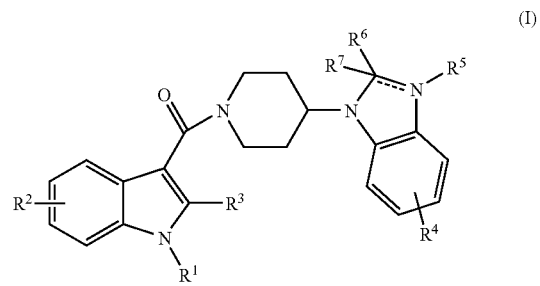

wherein the residues $R^1$ to $R^7$ are as defined herein. The invention further relates to pharmaceutical compositions containing such compounds, their use in treating dysmenorrhea, hypertension, chronic heart failure, inappropriate secretion of vasopressin, liver cirrhosis, nephritic syndrome, obsessive compulsive disorder, anxiety and depressive disorders, and methods of preparation thereof.

8 Claims, No Drawings

INDOL-3-YL-CORBONYL-PIPERIDIN-BENZOIMIDAZOL DERIVATIVES

PRIORITY TO RELATED APPLICATIONS

This application claims the benefit of European Application No. 05106695.9, filed Jul. 21, 2005, which is hereby incorporated by reference in its entirety.

BACKGROUND OF THE INVENTION

Vasopressin is a 9 amino acid peptide mainly produced by the paraventricular nucleus of the hypothalamus. Three vasopressin receptors, all belonging to the class I G-protein coupled receptors, are known. The V1a receptor is expressed in the brain, liver, vascular smooth muscle, lung, uterus and testis, the V1b or V3 receptor is expressed in the brain and pituitary gland, the V2 receptor is expressed in the kidney where it regulates water excretion and mediates the antidiuretic effects of vasopressin.

In the periphery vasopressin acts as a neurohormone and stimulates vasoconstriction, glycogenolysis and antidiuresis. In the brain vasopressin acts as a neuromodulator and is elevated in the amygdala during stress (Ebner, K., C. T. Wotjak, et al. (2002). "Forced swimming triggers vasopressin release within the amygdala to modulate stress-coping strategies in rats." Eur J Neurosci 15(2): 384-8). The V1a receptor is extensively expressed in the brain and particularly in limbic areas like the amygdala, lateral septum and hippocampus which are playing an important role in the regulation of anxiety. Indeed V1a knock-out mouse show a reduction in anxiety behavior in the plus-maze, open field and light-dark box (Bielsky, I. F., S. B. Hu, et al. (2003). "Profound Impairment in Social Recognition and Reduction in Anxiety-Like Behavior in Vasopressin V1a Receptor Knockout Mice." Neuropsychopharmacology). The downregulation of the V1a receptor using antisense oligonucleotide injection in the septum also causes a reduction in anxiety behavior (Landgraf, R., R. Gerstberger, et al. (1995). "V1 vasopressin receptor antisense oligodeoxynucleotide into septum reduces vasopressin binding, social discrimination abilities, and anxiety-related behavior in rats." Regul Pept 59(2): 229-39).

The V1a receptor is also mediating the cardiovascular effects of vasopressin in the brain by centrally regulating blood pressure and heart rate in the solitary tract nucleus (Michelini, L. C. and M. Morris (1999). "Endogenous vasopressin modulates the cardiovascular responses to exercise." Ann NY Acad Sci 897: 198-211). In the periphery it induces the contraction of vascular smooth muscles and chronic inhibition of the V1a receptor improves hemodynamic parameters in myocardial infarcted rats (Van Kerckhoven, R., I. Lankhuizen, et al. (2002). "Chronic vasopressin V(1A) but not V(2) receptor antagonism prevents heart failure in chronically infarcted rats." Eur J Pharmacol 449(1-2): 135-41).

Thus vasopressin receptor antagonists are useful as therapeutics in the conditions of dysmenorrhea, hypertension, chronic heart failure, inappropriate secretion of vasopressin, liver cirrhosis, nephrotic syndrome, obsessive compulsive disorder, anxiety and depressive disorders.

SUMMARY OF THE INVENTION

The present invention provides compounds of formula (I):

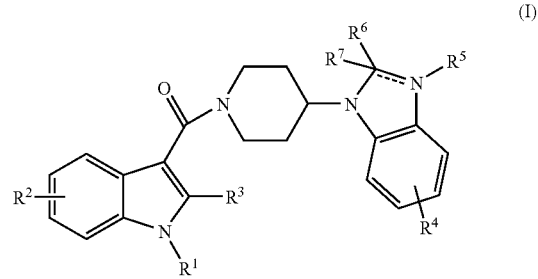

wherein the dotted line represents an optional double bond;
$R^1$ is H,
$C_{1-6}$-alkyl optionally substituted by CN,
aryl, 5 or 6 membered heteroaryl or sulfonylaryl each of which is optionally substituted by one or more B,
—$(CH_2)_m$—$R^a$ wherein $R^a$ is:
CN,
$OR^i$,
$NR^iR^{ii}$, or
$C_{3-6}$-cycloalkyl, 4 to 7 membered-heterocycloalkyl, aryl, or 5 or 6 membered heteroaryl each of which is optionally substituted by one or more B,
or —$(CH_2)_n$—(CO)—$R^b$ or —$(CH_2)_n$—$(SO_2)$—$R^b$, wherein $R^b$ is:
$C_{1-6}$-alkyl,
$C_{1-6}$-alkoxy,
$C_{3-6}$-cycloalkyl,
—$(CH_2)_m$—$NR^{iii}R^{iv}$,
$NR^iR^{ii}$, or
$C_{3-6}$-cycloalkyl, 4 to 7 membered-heterocycloalkyl, aryl, or 5 or 6 membered heteroaryl each of which is optionally substituted by one or more B,
or $R^1$ and $R^3$ together with the indole ring to which they are attached form a 5 or 6 membered heterocycloalkyl which is optionally substituted by =O;
there is one or more $R^2$, wherein each $R^2$ is the same or different,
$R^2$ is one or more H, OH, halo, CN, nitro, $C_{1-6}$-alkyl optionally substituted by —$NR^{iii}R^{iv}$, $C_{1-6}$-alkoxy, —O—$CH_2$—$C_{2-6}$-alkenyl, or benzyloxy,
or two $R^2$ together with the indole ring to which they are attached form an oxo or dioxo bridge;
$R^3$ is H,
halo,
—(CO)—$R^c$, wherein $R^c$ is:
$C_{1-6}$-alkyl,
—$(CH_2)_n$—$NR^iR^{ii}$,
—$(CH_2)_n$—$NR^{iii}R^{iv}$, or
5 or 6 membered heterocycloalkyl optionally substituted by $C_{1-6}$-alkyl, or $C_{1-6}$-alkyl or aryl, each of which is optionally substituted by
halo,
—O(CO)—$C_{1-6}$-alkyl, or
—NH(CO)$R^d$, wherein $R^d$ is $C_{1-6}$-alkyl optionally substituted by halo or nitro, or $R^d$ is aryl or a 5 or 6 membered heteroaryl, each of which is optionally substituted by halo, nitro, $C_{1-6}$-alkyl or $C_{1-6}$-haloalkyl;

there is one or more $R^4$, wherein each $R^4$ is the same or different, $R^4$ is one or more H, halo, $C_{1-6}$-alkyl or $C_{1-6}$-alkoxy or two $R^4$ together with the phenyl ring to which they are attached form an oxo or dioxo bridge;

$R^5$ is H, $C_{1-6}$-alkyl, —$(CH_2)_m$—$NR^iR^{ii}$, aryl, or —$(CH_2)_n$—(CO)—$R^b$ wherein $R^b$ is $NR^iR^{ii}$ or 4 to 7 membered-heterocycloalkyl, when the dotted line does not represent a double bond, or $R^5$ is absent when the dotted line represents a double bond;

$R^6$ is absent when the dotted line represents a double bond;

$R^7$ is H,

Cl, or $NR^eR^f$, wherein $R^e$ and $R^f$ are each independently H or $C_{1-6}$-alkyl or $R^e$ and $R^f$ together with the nitrogen atom to which they are attached form a 5 or 6 membered heterocycloalkyl which is optionally substituted by $C_{1-6}$-alkyl, or $R^6$ and $R^7$ together form a C=O group when the dotted line does not represent a double bond;

B is halo, CN, $NR^iR^{ii}$, $C_{1-6}$-alkyl optionally substituted by CN, halo or $C_{1-6}$-alkoxy, $C_{1-6}$-alkoxy, $C_{1-6}$-haloalkoxy, $C_{3-6}$-cycloalkyl, —C(O)O—$C_{1-6}$-alkyl, —C(O)$NR^iR^{ii}$, —C(O)—$C_{1-6}$-alkyl, —$S(O)_2$—$C_{1-6}$-alkyl, —$S(O)_2$—$NR^iR^{ii}$, $(CR^{iii}R^{iv})_n$-phenyl, or $(CR^{iii}R^{iv})_n$-5 or 6 membered heteroaryl wherein the phenyl or 5 or 6 membered heteroaryl moiety is optionally substituted by one or more substituent(s) selected from the group consisting of:

halo, CN, $NR^iR^{ii}$, $C_{1-6}$-alkyl optionally substituted by CN or $C_{1-6}$-alkoxy, $C_{1-6}$-alkoxy, $C_{1-6}$-haloalkoxy, $C_{3-6}$-cycloalkyl, —C(O)O—$C_{1-6}$-alkyl, —C(O)—$NR^iR^{ii}$, —C(O)—$C_{1-6}$-alkyl, —$S(O)_2$—$C_{1-6}$-alkyl, and —$S(O)_2$—$NR^iR^{ii}$;

$R^i$ and $R^{ii}$ are each independently H, $C_{1-6}$-alkyl, $C_{1-6}$-alkyl-$NR^{iii}R^{iv}$, —(CO)O—$C_{1-6}$-alkyl, —C(O)—$NR^{iii}R^{iv}$, —C(O)—$C_{1-6}$-alkyl, —$S(O)_2$—$C_{1-6}$-alkyl or —$S(O)_2$—$NR^{iii}R^{iv}$;

$R^{iii}$ and $R^{iv}$ are H or $C_{1-6}$-alkyl;

m is 1 to 6; and n is 0 to 4;

and pharmaceutically acceptable salts thereof.

The compounds of formula (I) can contain asymmetric carbon atoms. Accordingly, the present invention includes all stereoisomeric forms of the compounds of formula I, including each of the individual enantiomers and mixtures thereof.

Compounds of formula (I) have good activity on the V1a receptor. Therefore, the invention further provides methods for treating dysmenorrhea, hypertension, chronic heart failure, inappropriate secretion of vasopressin, liver cirrhosis, nephrotic syndrome, obsessive compulsive disorder, anxiety and depressive disorders by administering a pharmaceutical composition comprising a therapeutically effective amount of a compound of formula I or a pharmaceutically acceptable salt thereof and a pharmaceutically acceptable carrier.

The preferred indications with regard to the present invention are the treatment of anxiety and depressive disorders.

DETAILED DESCRIPTION OF THE INVENTION

The following definitions of general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "aryl" means a monovalent cyclic aromatic hydrocarbon moiety consisting of a mono-, bi- or tricyclic aromatic ring system. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, as well as those specifically illustrated by the examples herein below. Substituents for aryl include but are not limited to halogen, $C_{1-6}$-alkyl, $C_{1-6}$-alkoxy. Preferred aryl are phenyl and naphthyl and still preferably phenyl.

The term "$C_{1-6}$-alkyl" denotes a saturated straight- or branched-chain hydrocarbon group containing from 1 to 6 carbon atoms, for example, methyl, ethyl, propyl, isopropyl, n-butyl, i-butyl, 2-butyl, t-butyl as well as those groups specifically illustrated by the examples herein below. Preferred $C_{1-6}$-alkyl groups are $C_{1-4}$-groups, i.e. with 1-4 carbon atoms.

The term "$C_{1-6}$-alkoxy" denotes a group wherein the alkyl residue is as defined above, which is attached via an oxygen atom. Preferred $C_{1-6}$-alkoxy groups are methoxy and ethoxy as well as those specifically illustrated by the examples herein below.

The term "$C_{2-6}$-alkenyl" denotes a carbon chain of 2 to 6 carbon atoms comprising a double bond in its chain. $C_{2-6}$-alkenyl groups include ethenyl, propen-1-yl, propen-2-yl, buten-1-yl, buten-3-yl, penten-1-yl, penten-2-yl, penten-3-yl, penten-4-yl, hexen-1-yl, hexen-2-yl, hexen-3-yl, hexen-4-yl and hexen-5-yl, as well as those specifically illustrated by the examples herein below.

The term "benzyloxy" denotes a benzyl group attached via an oxygen atom.

The term "halogen" or "halo" denotes chlorine (Cl), iodine (I), fluorine (F) and bromine (Br).

The term "$C_{1-6}$-haloalkyl" denotes a $C_{1-6}$-alkyl group as defined above which is substituted by one or more halogen atom. Examples of $C_{1-6}$-haloalkyl include, but are not limited to, methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Preferred $C_{1-6}$-haloalkyl are difluoro- or trifluoro-methyl or ethyl.

"$C_{1-6}$-haloalkoxy" denotes a $C_{1-6}$-alkoxy group as defined above which is substituted by one or more halogen atom. Examples of $C_{1-6}$-haloalkoxy include, but are not limited to, methoxy or ethoxy, substituted by one or more Cl, F, Br or I atom(s) as well as those groups specifically illustrated by the examples herein below. Preferred $C_{1-6}$-haloalkoxy are difluoro- or trifluoro-methoxy or ethoxy.

The term "$C_{3-6}$-cycloalkyl" denotes a monovalent or divalent saturated carbocyclic moiety consisting of a monocyclic ring. Cycloalkyl can optionally be substituted with one, two, three or four substituents, wherein each substituent is independently hydroxy, $C_{1-6}$-alkyl, $C_{1-6}$-alkoxy, halogen, amino, unless otherwise specifically indicated. Examples of cycloalkyl moieties include optionally substituted cyclopropyl, optionally substituted cyclobutyl, optionally substituted cyclopentyl and optionally substituted cyclohexyl as well as those specifically illustrated by the examples herein below.

The term "4 to 7 membered heterocycloalkyl" means a monovalent saturated moiety, consisting of one ring of 4 to 7 atoms as ring members, including one, two, or three heteroatoms chosen from nitrogen, oxygen or sulfur, the rest being carbon atoms. 4 to 7 membered heterocycloalkyl can optionally be substituted with one, two, three or four substituents, wherein each substituent is independently hydroxy, $C_{1-6}$-alkyl, $C_{1-6}$-alkoxy, $C_{1-6}$-thioalkyl, halo, $C_{1-6}$-haloalkyl, $C_{1-6}$-hydroxyalkyl, alkoxycarbonyl, amino, $C_{1-6}$-alkylamino, di($C_{1-6}$)alkylamino, aminocarbonyl, or carbonylamino, unless otherwise specifically indicated. Examples of heterocyclic moieties include, but are not limited to, optionally substituted oxetane, optionally substituted tetrahydro-furanyl, optionally substituted piperidinyl, optionally substituted pyrrolidinyl, optionally substituted morpholinyl, optionally substituted piperazinyl, and the like or those which are specifically exemplified herein. Substituents can be selected from $C_{1-6}$-alkyl, $C_{1-6}$-alkoxy, $C_{1-6}$-haloalkyl, halo, CN, OH, $NH_2$, as well as those substituents which are specifically illustrated in the examples hereinafter. Preferred 4 to 7 membered heterocycloalkyl are 5 to 6 membered heterocycloalkyl.

The term "5 or 6 membered heteroaryl" means an aromatic ring of 5 or 6 ring atoms as ring members containing one, two, or three ring heteroatoms selected from N, O, or S, the rest being carbon atoms. 5 or 6 heteroaryl can optionally be substituted with one, two, three or four substituents, wherein each substituent is independently hydroxy, $C_{1-6}$-alkyl, $C_{1-6}$-alkoxy, $C_{1-6}$-thioalkyl, halo, $C_{1-6}$-haloalkyl, $C_{1-6}$-hydroxyalkyl, alkoxycarbonyl, amino, $C_{1-6}$-alkylamino, di($C_{1-6}$)alkylamino, aminocarbonyl, or carbonylamino, unless otherwise specifically indicated. Examples of heteroaryl moieties include, but are not limited to, optionally substituted imidazolyl, optionally substituted oxazolyl, optionally substituted thiazolyl, optionally substituted pyrazinyl, optionally substituted pyrrolyl, optionally substituted pyrazinyl, optionally substituted pyridinyl, optionally substituted pyrimidinyl, optionally substituted furanyl, and those which are specifically exemplified herein.

The term "sulfonylaryl" denotes an aryl group as defined hereinabove which is attached via a sulfonyl group.

The expression "two $R^2$ together with the indole ring to which they are attached form an oxo or dioxo bridge" or "two $R^4$ together with the phenyl ring to which they are attached form an oxo or dioxo bridge" denotes an oxo or dioxo bridge of the following formulae:

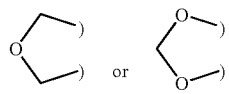

which bind two adjacent carbon atoms of the phenyl or indole ring of the compound of formula (I) to which either $R^2$ or $R^4$ is binding.

Examples of group illustrating the expression "$R^1$ and $R^3$ together with the indole ring to which they are attached form a 5 or 6 membered heterocycloalkyl which is optionally substituted by =O" are:

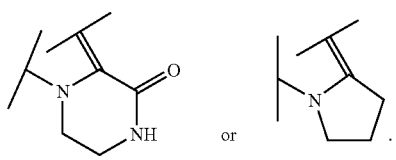

The expression "$R^e$ and $R^f$ together with the nitrogen atom to which they are attached form a 5 or 6 membered heterocycloalkyl which is optionally substituted by $C_{1-6}$-alkyl" denotes a 5 or 6 membered heterocycloalkyl group as defined hereinabove which is optionally substituted by one or more $C_{1-6}$-alkyl as defined hereinabove.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid, as well as those specifically illustrated by the examples herein below.

"Therapeutically effective amount" means an amount that is effective to prevent, alleviate or ameliorate symptoms of disease or prolong the survival of the subject being treated.

The present invention provides compounds of formula (I):

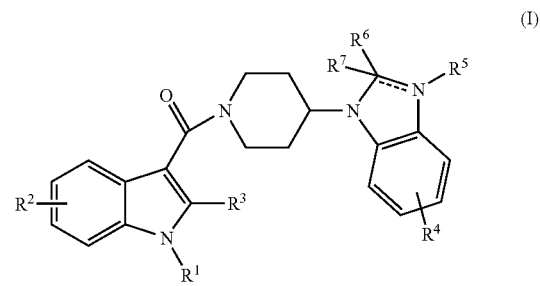

wherein the dotted line represents an optional double bond;
$R^1$ is H,
  $C_{1-6}$-alkyl optionally substituted by CN,
  aryl, 5 or 6 membered heteroaryl or sulfonylaryl each of which is optionally substituted by one or more B,
  —$(CH_2)_m$—$R^a$ wherein $R^a$ is:
    CN,
    $OR^i$,
    $NR^iR^{ii}$, or
    $C_{3-6}$-cycloalkyl, 4 to 7 membered-heterocycloalkyl, aryl, or 5 or 6 membered heteroaryl each of which is optionally substituted by one or more B,
  or —$(CH_2)_n$—(CO)—$R^b$ or —$(CH_2)_n$—$(SO_2)$—$R^b$, wherein $R^b$ is:
    $C_{1-6}$-alkyl,
    $C_{1-6}$-alkoxy,
    $C_{3-6}$-cycloalkyl,
    —$(CH_2)_m$—$NR^{iii}R^{iv}$,
    $NR^iR^{ii}$, or
    $C_{3-6}$-cycloalkyl, 4 to 7 membered-heterocycloalkyl, aryl, or 5 or 6 membered heteroaryl each of which is optionally substituted by one or more B,
or $R^1$ and $R^3$ together with the indole ring to which they are attached form a 5 or 6 membered heterocycloalkyl which is optionally substituted by =O;
there is one or more $R^2$, wherein each $R^2$ is the same or different,
$R^2$ is one or more H, OH, halo, CN, nitro, $C_{1-6}$-alkyl optionally substituted by —$NR^{iii}R^{iv}$, $C_{1-6}$-alkoxy, —O—$CH_2$—$C_{2-6}$-alkenyl, or benzyloxy,
  or two $R^2$ together with the indole ring to which they are attached form an oxo or dioxo bridge;

$R^3$ is H,
halo,
—(CO)—$R^c$, wherein $R^c$ is:
$C_{1-6}$-alkyl,
—(CH$_2$)$_n$—NR$^i$R$^{ii}$,
—(CH$_2$)$_n$—NR$^{iii}$R$^{iv}$, or
5 or 6 membered heterocycloalkyl optionally substituted by $C_{1-6}$-alkyl, or $C_{1-6}$-alkyl or aryl, each of which is optionally substituted by
halo,
—O(CO)—$C_{1-6}$-alkyl, or
—NH(CO)R$^d$, wherein R$^d$ is $C_{1-6}$-alkyl optionally substituted by halo or nitro, or R$^d$ is aryl or a 5 or 6 membered heteroaryl, each of which is optionally substituted by halo, nitro, $C_{1-6}$-alkyl or $C_{1-6}$-haloalkyl;
there is one or more $R^4$, wherein each $R^4$ is the same or different,
$R^4$ is one or more H, halo, $C_{1-6}$-alkyl or $C_{1-6}$-alkoxy or two $R^4$ together with the phenyl ring to which they are attached form an oxo or dioxo bridge;
$R^5$ is H, $C_{1-6}$-alkyl, (CH$_2$)$_m$—NR$^i$R$^{ii}$, aryl, or —(CH$_2$)$_n$—(CO)—R$^b$ wherein R$^b$ is NR$^i$R$^{ii}$ or 4 to 7 membered-heterocycloalkyl, when the dotted line does not represent a double bond,
or $R^5$ is absent when the dotted line represents a double bond;
$R^6$ is absent when the dotted line represents a double bond;
$R^7$ is H,
Cl, or
NR$^e$R$^f$, wherein R$^e$ and R$^f$ are each independently H or $C_{1-6}$-alkyl or R$^e$ and R$^f$ together with the nitrogen atom to which they are attached form a 5 or 6 membered heterocycloalkyl which is optionally substituted by $C_{1-6}$-alkyl,
or $R^6$ and $R^7$ together form a C=O group when the dotted line does not represent a double bond;
B is halo, CN, NR$^i$R$^{ii}$, $C_{1-6}$-alkyl optionally substituted by CN, halo or $C_{1-6}$-alkoxy, $C_{1-6}$-alkoxy, $C_{1-6}$-haloalkoxy, $C_{3-6}$-cycloalkyl, —C(O)O—$C_{1-6}$-alkyl, —C(O)NR$^i$R$^{ii}$, —C(O)—$C_{1-6}$-alkyl, —S(O)$_2$—$C_{1-6}$-alkyl, —S(O)$_2$—NR$^i$R$^{ii}$, (CR$^{iii}$R$^{iv}$)$_n$-phenyl, or (CR$^{iii}$R$^{iv}$)$_n$-5 or 6 membered heteroaryl wherein the phenyl or 5 or 6 membered heteroaryl moiety is optionally substituted by one or more substituent(s) selected from the group consisting of:
halo, CN, NR$^i$R$^{ii}$, $C_{1-6}$-alkyl optionally substituted by CN or $C_{1-6}$-alkoxy, $C_{1-6}$-alkoxy, $C_{1-6}$-haloalkoxy, $C_{3-6}$-cycloalkyl, —C(O)O—$C_{1-6}$-alkyl, —C(O)—NR$^i$R$^{ii}$, —C(O)—$C_{1-6}$-alkyl, —S(O)$_2$—$C_{1-6}$-alkyl, and —S(O)$_2$—NR$^i$R$^{ii}$;
$R^i$ and $R^{ii}$ are each independently H, $C_{1-6}$-alkyl, $C_{1-6}$-alkyl-NR$^{iii}$R$^{iv}$, —(CO)O—$C_{1-6}$-alkyl, —C(O)—NR$^{iii}$R$^{iv}$, —C(O)—$C_{1-6}$-alkyl, —S(O)$_2$—$C_{1-6}$-alkyl or —S(O)$_2$—NR$^{iii}$R$^{iv}$;
$R^{iii}$ and $R^{iv}$ are H or $C_{1-6}$-alkyl;
m is 1 to 6; and
n is 0 to 4;

and pharmaceutically acceptable salts thereof.

In a certain embodiment, the compounds according to the invention are those of formula (I) wherein:
the dotted line represents an optional double bond;
$R^5$ is H, $C_{1-6}$-alkyl, —(CH$_2$)$_m$—NR$^i$R$^{ii}$ or aryl when the dotted does not represent a double bond or is absent when the dotted line represents a double bond;
and $R^1$, $R^2$, $R^3$, $R^4$, $R^6$ and $R^7$ are as defined above, as well as pharmaceutically acceptable salts thereof.

In a further embodiment, the compounds according to the invention are those of formula (I) wherein:
$R^1$ is H
$C_{1-6}$-alkyl optionally substituted by CN or $C_{1-6}$-alkoxy,
aryl,
5 or 6 membered heteroaryl,
sulfonylaryl,
—(CH$_2$)$_m$—R$^a$ wherein R$^a$ is $C_{3-6}$-cycloalkyl, 5 or 6 membered-heterocycloalkyl, aryl, or 5 or 6 membered heteroaryl each of which is optionally substituted by one or more substituents selected from the group consisting of:
halo, CN, $C_{1-6}$-alkyl, $C_{1-6}$-alkoxy, $C_{1-6}$-haloalkoxy, —C(O)O—$C_{1-6}$-alkyl and phenyl optionally substituted by halo, $C_{1-6}$-alkyl, $C_{1-6}$-haloalkyl or $C_{1-6}$-alkoxy,
—(CH$_2$)$_m$—NR$^i$R$^{ii}$, or
—(CH$_2$)$_n$—(CO)—R$^b$, wherein R$^b$ is aryl or 5 or 6 membered-heterocycloalkyl;
there is one or more $R^2$, wherein each $R^2$ is the same or different,
$R^2$ is one or more H, halo, CN, nitro, $C_{1-6}$-alkyl, $C_{1-6}$-alkoxy, —O—CH$_2$—$C_{2-6}$-alkenyl, or benzyloxy, or two $R^2$ together with the indole ring to which they are attached form an oxo or dioxo bridge;
$R^3$ is H,
halo,
—(CO)—R$^c$, wherein R$^c$ is $C_{1-6}$-alkyl, 5 or 6 membered heterocycloalkyl optionally substituted by $C_{1-6}$-alkyl, or R$^c$ is —(CH$_2$)$_n$—NR$^i$R$^{ii}$,
$C_{1-6}$-alkyl or aryl, each of which is optionally substituted by
—O(CO)—$C_{1-6}$-alkyl,
or —NH(CO)R$^d$, wherein R$^d$ is $C_{1-6}$-alkyl optionally substituted by halo or nitro, or R$^d$ is aryl or a 5 or 6 membered heteroaryl, each of which is optionally substituted by halo, nitro, $C_{1-6}$-alkyl or $C_{1-6}$-haloalkyl;
there is one or more $R^4$, wherein each $R^4$ is the same or different,
$R^4$ is one or more H, halo, $C_{1-6}$-alkyl or $C_{1-6}$-alkoxy or two $R^4$ together with the phenyl ring to which they are attached form an oxo or dioxo bridge;
$R^5$ is H, $C_{1-6}$-alkyl, —(CH$_2$)$_m$—NR$^i$R$^{ii}$ or aryl, when the dotted line does not represent a double bond,
or is absent when the dotted line represents a double bond;
$R^6$ is absent when the dotted line represents a double bond;
$R^7$ is H,
Cl, or
NR$^e$R$^f$, wherein R$^e$ and R$^f$ are each independently H or $C_{1-6}$-alkyl or R$^e$ and R$^f$ together with the nitrogen atom to which they are attached form a 5 or 6 membered heterocycloalkyl,
or $R^6$ and $R^7$ together form a C=O group when the dotted line does not represent a double bond;
$R^i$ and $R^{ii}$ are each independently selected from H, $C_{1-6}$-alkyl and —(CO)O—$C_{1-6}$-alkyl;
m is 1 to 6; and
n is 0 to 4;

and pharmaceutically acceptable salts thereof.

Also encompassed by the invention are compounds of formula (I) of formula (I-a):

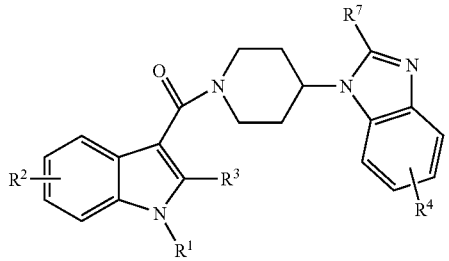

(I-a)

wherein $R^1$ to $R^4$ and $R^7$ are as defined hereinabove for formula (I).

Further encompassed by the invention are the compounds of formula (I-a) wherein:
$R^1$ is H,
  $C_{1-6}$-alkyl optionally substituted by CN or $C_{1-6}$-alkoxy,
  aryl,
  5 or 6 membered heteroaryl,
  sulfonylaryl,
  —$(CH_2)_m$—$R^a$ wherein $R^a$ is $C_{3-6}$-cycloalkyl, 5 or 6 membered-heterocycloalkyl, aryl, or 5 or 6 membered heteroaryl each of which is optionally substituted by one or more substituents selected from the group consisting of:
    halo, CN, $C_{1-6}$-alkyl, $C_{1-6}$-alkoxy, $C_{1-6}$-haloalkoxy, —C(O)O—$C_{1-6}$-alkyl and phenyl optionally substituted by halo, $C_{1-6}$-alkyl, $C_{1-6}$-haloalkyl or $C_{1-6}$-alkoxy,
  —$(CH_2)_m$—$NR^iR^{ii}$, or
  —$(CH_2)_n$—(CO)—$R^b$, wherein $R^b$ is aryl or 5 or 6 membered-heterocycloalkyl;
there is one or more $R^2$, wherein each $R^2$ is the same or different,
$R^2$ is one or more H, halo, CN, nitro, $C_{1-6}$-alkyl, $C_{1-6}$-alkoxy, —O—$CH_2$—$C_{2-6}$-alkenyl, or benzyloxy, or two $R^2$ together with the indole ring to which they are attached form an oxo or dioxo bridge;
$R^3$ is H,
  halo,
  —(CO)—$R^c$, wherein $R^c$ is $C_{1-6}$-alkyl, 5 or 6 membered heterocycloalkyl optionally substituted by $C_{1-6}$-alkyl, or $R^c$ is —$(CH_2)_n$—$NR^iR^{ii}$, or
  $C_{1-6}$-alkyl or aryl, each of which is optionally substituted by
    —O(CO)—$C_{1-6}$-alkyl, or
    —NH(CO)$R^d$, wherein $R^d$ is $C_{1-6}$-alkyl optionally substituted by halo or nitro, or $R^d$ is aryl or a 5 or 6 membered heteroaryl, each of which is optionally substituted by halo, nitro, $C_{1-6}$-alkyl or $C_{1-6}$-haloalkyl;
there is one or more $R^4$, wherein each $R^4$ is the same or different,
$R^4$ is one or more H, halo, $C_{1-6}$-alkyl or $C_{1-6}$-alkoxy or two $R^4$ together with the phenyl ring to which they are attached form an oxo or dioxo bridge;
$R^7$ is H,
  Cl, or
  $NR^eR^f$, wherein $R^e$ and $R^f$ are each independently H or $C_{1-6}$-alkyl or $R^e$ and $R^f$ together with the nitrogen atom to which they are attached form a 5 or 6 membered heterocycloalkyl which is optionally is optionally substituted by $C_{1-6}$-alkyl,
$R^i$ and $R^{ii}$ are each independently selected from H, $C_{1-6}$-alkyl and —(CO)O—$C_{1-6}$-alkyl;

m is 1 to 6; and
n is 0 to 4;

and pharmaceutically acceptable salts thereof.
Preferred compounds of formula (I-a) are those compounds of formula (I-a), wherein:
$R^1$ is H,
  $C_{1-6}$-alkyl optionally substituted by CN, or
  —$(CH_2)_m$—$R^a$ wherein $R^a$ is aryl, which is optionally substituted by one or more substituent selected from the group consisting of:
    halo, CN, $C_{1-6}$-alkyl, $C_{1-6}$-alkoxy, $C_{1-6}$-haloalkoxy, —C(O)O—$C_{1-6}$-alkyl and phenyl optionally substituted by halo, $C_{1-6}$-alkyl, $C_{1-6}$-haloalkyl or $C_{1-6}$-alkoxy,
there is one or more $R^2$, wherein each $R^2$ is the same or different,
$R^2$ is one or more H, halo or $C_{1-6}$-alkoxy;
$R^3$ is H,
  —(CO)—$R^c$, wherein $R^c$ is $C_{1-6}$-alkyl or 5 or 6 membered heterocycloalkyl optionally substituted by $C_{1-6}$-alkyl, or
  $C_{1-6}$-alkyl;
$R^4$ is H;
$R^7$ is Cl, or
  $NR^eR^f$, wherein $R^e$ and $R^f$ are each independently H or $C_{1-6}$-alkyl or $R^e$ and $R^f$ together with the nitrogen atom to which they are attached form a 5 or 6 membered heterocycloalkyl which is optionally substituted by $C_{1-6}$-alkyl, and
m is 1 to 6;

and pharmaceutically acceptable salts thereof, for example the following compounds:
(1-Benzyl-2-methyl-1H-indol-3-yl)-[4-(2-chloro-benzoimidazol-1-yl)-piperidin-1-yl]-methanone;
(1-Benzyl-2-methyl-1H-indol-3-yl)-{4-[2-(4-methyl-piperazin-1-yl)-benzoimidazol-1-yl]-piperidin-1-yl}-methanone;
(1-Benzyl-2-methyl-1H-indol-3-yl)-[4-(2-morpholin-4-yl-benzoimidazol-1-yl)-piperidin-1-yl]-methanone;
(1-Benzyl-2-methyl-1H-indol-3-yl)-[4-(2-piperidin-1-yl-benzoimidazol-1-yl)-piperidin-1-yl]-methanone;
[4-(2-Chloro-benzoimidazol-1-yl)-piperidin-1-yl]-(2-methyl-1H-indol-3-yl)-methanone;
[4-(2-Dimethylamino-benzoimidazol-1-yl)-piperidin-1-yl]-(2-methyl-1H-indol-3-yl)-methanone; and
[4-(2-Methylamino-benzoimidazol-1-yl)-piperidin-1-yl]-(2-methyl-1H-indol-3-yl)-methanone.

Also encompassed by the invention are compounds of formula (I) having formula (I-b):

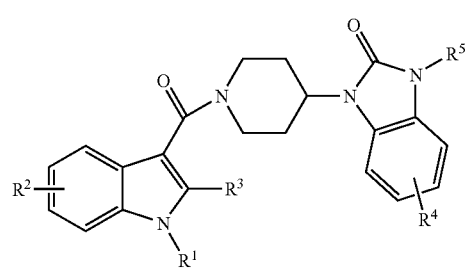

(I-b)

wherein $R^1$ to $R^5$ are as defined hereinabove for formula (I).
Further encompassed by the invention are the compounds of formula (I-b) wherein:
$R^1$ is H,
  $C_{1-6}$-alkyl optionally substituted by CN or $C_{1-6}$-alkoxy,
  aryl, 5 or 6 membered heteroaryl,
sulfonylaryl,
—$(CH_2)_m$—$R^a$ wherein $R^a$ is $C_{3-6}$-cycloalkyl, 5 or 6 membered-heterocycloalkyl, aryl, or 5 or 6 membered heteroaryl each of which is optionally substituted by one or more substituents selected from the group consisting of:
halo, CN, $C_{1-6}$-alkyl, $C_{1-6}$-alkoxy, $C_{1-6}$-haloalkoxy, —C(O)O—$C_{1-6}$-alkyl and phenyl optionally substituted by halo, $C_{1-6}$-alkyl, $C_{1-6}$-haloalkyl or $C_{1-6}$-alkoxy,
—$(CH_2)_m$—$NR^iR^{ii}$, or
—$(CH_2)_n$—(CO)—$R^b$ or —$(CH_2)_n$—$(SO_2)$—$R^b$, wherein $R^b$ is:
$NR^iR^{ii}$, or
4 to 7 membered-heterocycloalkyl, aryl, or 5 or 6 membered heteroaryl each of which is optionally substituted by one or more halo, $C_{1-6}$-alkyl optionally substituted by CN, halo or $C_{1-6}$-alkoxy, $C_{1-6}$-alkoxy, $C_{1-6}$-haloalkoxy or $(CR^{iii}R^{iv})_n$-phenyl;
there is one or more $R^2$, wherein each $R^2$ is the same or different,
$R^2$ is one or more H, halo, CN, nitro, $C_{1-6}$-alkyl, $C_{1-6}$-alkoxy, —O—$CH_2$—$C_{2-6}$-alkenyl, benzyloxy, or two $R^2$ together with the indole ring to which they are attached form an oxo or dioxo bridge;
$R^3$ is H,
halo,
—(CO)—$R^c$, wherein $R^c$ is $C_{1-6}$-alkyl, 5 or 6 membered heterocycloalkyl optionally substituted by $C_{1-6}$-alkyl, or $R^c$ is —$(CH_2)_n$—$NR^iR^{ii}$, or
$C_{1-6}$-alkyl or aryl, each of which is optionally substituted by
—O(CO)—$C_{1-6}$-alkyl,
or —NH(CO)$R^d$, wherein $R^d$ is $C_{1-6}$-alkyl optionally substituted by halo or nitro, or $R^d$ is aryl or a 5 or 6 membered heteroaryl, each of which is optionally substituted by halo, nitro, $C_{1-6}$-alkyl or $C_{1-6}$-haloalkyl;
there is one or more $R^4$, wherein each $R^4$ is the same or different,
$R^4$ is one or more H, halo, $C_{1-6}$-alkyl or $C_{1-6}$-alkoxy or two $R^4$ together with the phenyl ring to which they are attached form an oxo or dioxo bridge;
$R^5$ is H, $C_{1-6}$-alkyl, —$(CH_2)_m$—$NR^iR^{ii}$, aryl, or —$(CH_2)_n$—(CO)—$R^b$ wherein $R^b$ is $NR^iR^{ii}$ or 4 to 7 membered-heterocycloalkyl;
$R^i$ and $R^{ii}$ are each independently selected from H, $C_{1-6}$-alkyl and —(CO)O—$C_{1-6}$-alkyl;
$R^{iii}$ and $R^{iv}$ are H or $C_{1-6}$-alkyl;
m is 1 to 6; and
n is 0 to 4;

and pharmaceutically acceptable salts thereof.

Preferred compounds of formula (I-b) are those compounds of formula (I-b), wherein:
$R^1$ is H,
$C_{1-6}$-alkyl optionally substituted by CN,
—$(CH_2)_m$—$R^a$ wherein $R^a$ is aryl, which is optionally substituted by one or more substituents selected from the group consisting of:
halo, CN, $C_{1-6}$-alkyl, $C_{1-6}$-alkoxy, $C_{1-6}$-haloalkoxy, —C(O)O—$C_{1-6}$-alkyl and phenyl optionally substituted by halo, $C_{1-6}$-alkyl, $C_{1-6}$-haloalkyl or $C_{1-6}$-alkoxy,
—$(CH_2)_m$—$NR^iR^{ii}$, or
—$(CH_2)_n$—(CO)—$R^b$ or —$(CH_2)_n$—$(SO_2)$—$R^b$, wherein $R^b$ is:
$NR^iR^{ii}$, or
4 to 7 membered-heterocycloalkyl, aryl, or 5 or 6 membered heteroaryl each of which is optionally substituted by one or more halo, $C_{1-6}$-alkyl optionally substituted by CN, halo or $C_{1-6}$-alkoxy, $C_{1-6}$-alkoxy, $C_{1-6}$-haloalkoxy or $(CR^{iii}R^{iv})_n$-phenyl;
there is one or more $R^2$, wherein each $R^2$ is the same or different,
$R^2$ is one or more H, halo or $C_{1-6}$-alkoxy;
$R^3$ is H,
—(CO)—$R^c$, wherein $R^c$ is $C_{1-6}$-alkyl or 5 or 6 membered heterocycloalkyl optionally substituted by $C_{1-6}$-alkyl, or $C_{1-6}$-alkyl;
$R^4$ is H;
$R^5$ is H, $C_{1-6}$-alkyl, —$(CH_2)_m$—$NR^iR^{ii}$, aryl, or —$(CH_2)_n$—(CO)—$R^b$ wherein $R^b$ is $NR^iR^{ii}$ or 4 to 7 membered-heterocycloalkyl;
$R^i$ and $R^{ii}$ are each independently selected from H, $C_{1-6}$-alkyl and —(CO)O—$C_{1-6}$-alkyl;
$R^{iii}$ and $R^{iv}$ are H or $C_{1-6}$-alkyl;
m is 1 to 6; and
n is 0 to 4;

as well as pharmaceutically acceptable salts thereof.

In further embodiments of the invention, the compounds of formula (I-b) wherein:
$R^1$ is H,
$C_{1-6}$-alkyl optionally substituted by CN or $C_{1-6}$-alkoxy,
aryl,
5 or 6 membered heteroaryl,
sulfonylaryl,
—$(CH_2)_m$—$R^a$ wherein $R^a$ is $C_{3-6}$-cycloalkyl, 5 or 6 membered-heterocycloalkyl, aryl, or 5 or 6 membered heteroaryl each of which is optionally substituted by one or more substituents selected from the group consisting of:
halo, CN, $C_{1-6}$-alkyl, $C_{1-6}$-alkoxy, $C_{1-6}$-haloalkoxy, —C(O)O—$C_{1-6}$-alkyl and phenyl optionally substituted by halo, $C_{1-6}$-alkyl, $C_{1-6}$-haloalkyl or $C_{1-6}$-alkoxy,
—$(CH_2)_m$—$NR^iR^{ii}$, or
—$(CH_2)_n$—(CO)—$R^b$, wherein $R^b$ is aryl or 5 or 6 membered-heterocycloalkyl;
there is one or more $R^2$, wherein each $R^2$ is the same or different,
$R^2$ is one or more H, halo, CN, nitro, $C_{1-6}$-alkyl, $C_{1-6}$-alkoxy, —O—$CH_2$—$C_{2-6}$-alkenyl, or benzyloxy, or two $R^2$ together with the indole ring to which they are attached form an oxo or dioxo bridge;
$R^3$ is H,
halo,
—(CO)—$R^c$, wherein $R^c$ is $C_{1-6}$-alkyl, 5 or 6 membered heterocycloalkyl optionally substituted by $C_{1-6}$-alkyl, or $R^c$ is —$(CH_2)_n$—$NR^iR^{ii}$, or
$C_{1-6}$-alkyl or aryl, each of which is optionally substituted by
—O(CO)—$C_{1-6}$-alkyl, or
—NH(CO)$R^d$, wherein $R^d$ is $C_{1-6}$-alkyl optionally substituted by halo or nitro, or $R^d$ is aryl or a 5 or 6 membered heteroaryl, each of which is optionally substituted by halo, nitro, $C_{1-6}$-alkyl or $C_{1-6}$-haloalkyl;
there is one or more $R^4$, wherein each $R^4$ is the same or different,
$R^4$ is one or more H, halo, $C_{1-6}$-alkyl or $C_{1-6}$-alkoxy or two $R^4$ together with the phenyl ring to which they are attached form an oxo or dioxo bridge;
$R^5$ is H, $C_{1-6}$-alkyl, —$(CH_2)_m$—$NR^iR^{ii}$ or aryl;
$R^i$ and $R^{ii}$ are each independently selected from H, $C_{1-6}$-alkyl and —(CO)O—$C_{1-6}$-alkyl;
m is 1 to 6; and
n is 0 to 4;

and pharmaceutically acceptable salts thereof.

A further embodiment of the invention encompasses compounds of formula (I-b), wherein:
$R^1$ is H,
  $C_{1-6}$-alkyl optionally substituted by CN, or
  —(CH$_2$)$_m$—$R^a$ wherein $R^a$ is aryl, which is optionally substituted by one or more substituents selected from the group consisting of:
    halo, CN, $C_{1-6}$-alkyl, $C_{1-6}$-alkoxy, $C_{1-6}$-haloalkoxy, —C(O)O—$C_{1-6}$-alkyl and phenyl optionally substituted by halo, $C_{1-6}$-alkyl, $C_{1-6}$-haloalkyl or $C_{1-6}$-alkoxy,
there is one or more $R^2$, wherein each $R^2$ is the same or different,
$R^2$ is one or more H, halo or $C_{1-6}$-alkoxy;
$R^3$ is H,
  —(CO)—$R^c$, wherein $R^c$ is $C_{1-6}$-alkyl or 5 or 6 membered heterocycloalkyl optionally substituted by $C_{1-6}$-alkyl, or $C_{1-6}$-alkyl;
$R^4$ is H;
$R^5$ is H or $C_{1-6}$-alkyl; and
m is 1 to 6;

and pharmaceutically acceptable salts thereof.

The following examples are according to the invention:
1-[1-(1-Methyl-1H-indole-3-carbonyl)-piperidin-4-yl]-1,3-dihydro-benzoimidazol-2-one;
1-[1-(H-Indole-3-carbonyl)-piperidin-4-yl]-1,3-dihydro-benzoimidazol-2-one;
1-{-[2-(Pyrrolidine-1-carbonyl)-1H-indole-3-carbonyl]-piperidin-4-yl}-1,3-dihydro-benzoimidazol-2-one; and
1-{1-[6-Chloro-1-(3,5-difluoro-benzenesulfonyl)-1H-indole-3-carbonyl]-piperidin-4-yl}-1,3-dihydro-benzoimidazol-2-one.

Preferred are the following examples according to the invention:
1-[1-(1-Benzyl-1H-indole-3-carbonyl)-piperidin-4-yl]-1,3-dihydro-benzoimidazol-2-one;
1-[1-(1-Benzyl-2-methyl-1H-indole-3-carbonyl)-piperidin-4-yl]-3-methyl-1,3-dihydro-benzoimidazol-2-one;
1-[1-(2-Methyl-1H-indole-3-carbonyl)-piperidin-4-yl]-1,3-dihydro-benzoimidazol-2-one;
1-[1-(1-Isopropyl-6-methoxy-1H-indole-3-carbonyl)-piperidin-4-yl]-1,3-dihydro-benzoimidazol-2-one;
1-[1-(6-Fluoro-1-isopropyl-1H-indole-3-carbonyl)-piperidin-4-yl]-1,3-dihydro-benzoimidazol-2-one;
1-[1-(1-Isopropyl-1H-indole-3-carbonyl)-piperidin-4-yl]-1,3-dihydro-benzoimidazol-2-one;
1-[1-(1-Cyclohexylmethyl-1H-indole-3-carbonyl)-piperidin-4-yl]-1,3-dihydro-benzoimidazol-2-one;
1-{1-[6-Chloro-1-(3-fluoro-benzoyl)-1H-indole-3-carbonyl]-piperidin-4-yl}-1,3-dihydro-benzoimidazol-2-one;
1-(1-{6-Chloro-1-[2-(3-fluoro-phenyl)-2-oxo-ethyl]-1H-indole-3-carbonyl}-piperidin-4-yl)-1,3-dihydro-benzoimidazol-2-one;
1-{1-[6-Chloro-1-(2-fluoro-benzoyl)-1H-indole-3-carbonyl]-piperidin-4-yl}-1,3-dihydro-benzoimidazol-2-one;
1-{1-[6-Chloro-1-(2,3-difluoro-benzoyl)-1H-indole-3-carbonyl]-piperidin-4-yl}-1,3-dihydro-benzoimidazol-2-one;
1-{1-[6-Chloro-1-(3,5-difluoro-benzyl)-1H-indole-3-carbonyl]-piperidin-4-yl}-1,3-dihydro-benzoimidazol-2-one;
1-{1-[6-Chloro-1-(3,5-difluoro-benzoyl)-1H-indole-3-carbonyl]-piperidin-4-yl}-1,3-dihydro-benzoimidazol-2-one;
1-(1-{6-Chloro-1-[2-(3,4-difluoro-phenyl)-2-oxo-ethyl]-1H-indole-3-carbonyl}-piperidin-4-yl)-1,3-dihydro-benzoimidazol-2-one;
1-{1-[6-Chloro-1-(3,5-difluoro-phenyl)-1H-indole-3-carbonyl]-piperidin-4-yl}-1,3-dihydro-benzoimidazol-2-one;
1-{1-[6-Chloro-1-(piperidine-1-carbonyl)-1H-indole-3-carbonyl]-piperidin-4-yl}-1,3-dihydro-benzoimidazol-2-one;
1-{1-[6-Chloro-1-(2-oxo-2-piperidin-1-yl-ethyl)-1H-indole-3-carbonyl]-piperidin-4-yl}-3-(2-oxo-2-piperidin-1-yl-ethyl)-1,3-dihydro-benzoimidazol-2-one;
2-{3-[1-(6-Chloro-1-diethylcarbamoylmethyl-1H-indole-3-carbonyl)-piperidin-4-yl]-2-oxo-2,3-dihydro-benzoimidazol-1-yl}-N,N-diethyl-acetamide;
1-(1-{6-Chloro-1-[2-(3,5-difluoro-phenyl)-2-oxo-ethyl]-1H-indole-3-carbonyl}-piperidin-4-yl)-1,3-dihydro-benzoimidazol-2-one; and
1-(1-{6-Chloro-1-[2-(5-methyl-2-phenyl-oxazol-4-yl)-2-oxo-ethyl]-1H-indole-3-carbonyl}-piperidin-4-yl)-1,3-dihydro-benzoimidazol-2-one.

Most preferred are the following compounds according to the invention:
1-{1-[6-Chloro-1-(2-dimethylamino-ethyl)-1H-indole-3-carbonyl]-piperidin-4-yl}-1,3-dihydro-benzoimidazol-2-one;
1-(1-{6-Chloro-1-[2-(2-fluoro-phenyl)-2-oxo-ethyl]-1H-indole-3-carbonyl}-piperidin-4-yl)-1,3-dihydro-benzoimidazol-2-one;
2-{6-Chloro-3-[4-(2-oxo-2,3-dihydro-benzoimidazol-1-yl)-piperidine-1-carbonyl]-indol-1-yl}-N,N-dimethyl-acetamide;
1-[1-(6-Chloro-1-isopropyl-1H-indole-3-carbonyl)-piperidin-4-yl]-1,3-dihydro-benzoimidazol-2-one;
1-[1-(1-Benzyl-6-chloro-1H-indole-3-carbonyl)-piperidin-4-yl]-1,3-dihydro-benzoimidazol-2-one;
2-{5,6-Dichloro-3-[4-(2-oxo-2,3-dihydro-benzoimidazol-1-yl)-piperidine-1-carbonyl]-indol-1-yl}-N,N-dimethyl-acetamide;
1-[1-(1-Benzyl-2-methyl-1H-indole-3-carbonyl)-piperidin-4-yl]-3-(2-dimethylamino-ethyl)-1,3-dihydro-benzoimidazol-2-one;
1-[1-(6-Chloro-5-fluoro-1H-indole-3-carbonyl)-piperidin-4-yl]-1,3-dihydro-benzoimidazol-2-one;
2-{6-Chloro-5-methyl-3-[4-(2-oxo-2,3-dihydro-benzoimidazol-1-yl)-piperidine-1-carbonyl]-indol-1-yl}-N,N-dimethyl-acetamide;
1-(1-{6-Chloro-1-[2-(2,5-difluoro-phenyl)-2-oxo-ethyl]-1H-indole-3-carbonyl}-piperidin-4-yl)-1,3-dihydro-benzoimidazol-2-one;
1-[1-(6-Chloro-1H-indole-3-carbonyl)-piperidin-4-yl]-3-(2-dimethylamino-ethyl)-1,3-dihydro-benzoimidazol-2-one;
{6-Chloro-3-[4-(2-oxo-2,3-dihydro-benzoimidazol-1-yl)-piperidine-1-carbonyl]-indol-1-yl}-acetonitrile;
1-[1-(1-Benzyl-2-methyl-1H-indole-3-carbonyl)-piperidin-4-yl]-1,3-dihydro-benzoimidazol-2-one;
1-(1-{6-Chloro-1-[2-(2,4-difluoro-phenyl)-2-oxo-ethyl]-1H-indole-3-carbonyl}-piperidin-4-yl)-1,3-dihydro-benzoimidazol-2-one;
1-[1-(6-Chloro-1H-indole-3-carbonyl)-piperidin-4-yl]-1,3-dihydro-benzoimidazol-2-one;
1-{1-[6-Chloro-1-(3-fluoro-benzyl)-1H-indole-3-carbonyl]-piperidin-4-yl}-1,3-dihydro-benzoimidazol-2-one; and
1-{1-[2-(2-Methyl-butyryl)-1H-indole-3-carbonyl]-piperidin-4-yl}-1,3-dihydro-benzoimidazol-2-one.

The invention also encompasses the compounds of formula (I), (I-a) or (I-b), for a use in the prevention or treatment of dysmenorrhea, hypertension, chronic heart failure, inappropriate secretion of vasopressin, liver cirrhosis, nephrotic syndrome, obsessive compulsive disorder, anxiety and depressive disorders.

The invention also encompasses a pharmaceutical composition comprising a therapeutically effective amount of a compound of formula (I), (I-a) or (I-b), and a pharmaceutically acceptable carrier. Such pharmaceutical composition is useful for the treatment of dysmenorrhea, hypertension, chronic heart failure, inappropriate secretion of vasopressin, liver cirrhosis, nephrotic syndrome, obsessive compulsive disorder, anxiety and depressive disorders.

The invention also provides a method for preparing compositions of the invention which comprises bringing one or more compounds of formula I and/or pharmaceutically acceptable acid addition salts thereof and, if desired, one or more other therapeutically valuable substances into a galenical administration form together with one or more therapeutically inert carriers.

In a certain embodiment, the compounds of formula (I) according to the invention can be manufactured according to a process comprising reacting a compound of formula (II):

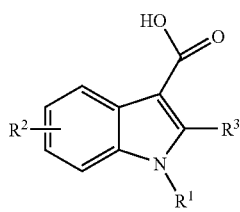

with a compound of formula (III):

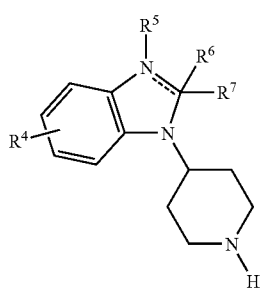

to obtain a compound of formula (I), wherein $R^1$ to $R^7$ are as defined hereinabove. This process is described in more detail with general scheme and procedure A.

In a certain embodiment, the compounds of formula (I) can be manufactured according to a process comprising reacting a compound of formula (IV):

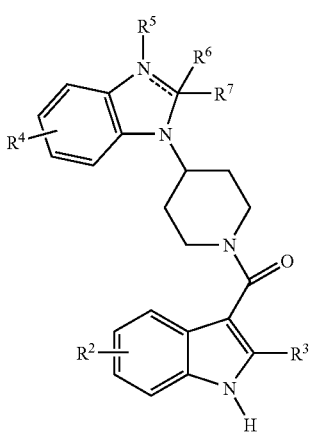

with a compound of formula $R^1$—X, to obtain a compound of formula (I), wherein $R^1$ to $R^7$ are as defined hereinabove. This process is described in detail with general scheme and procedure D.

In a certain embodiment, the compounds of formula (I-a) can be manufactured according to a process comprising reacting a compound of formula (I-a1):

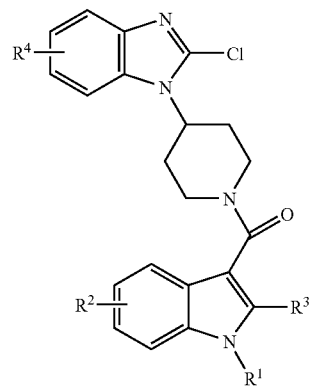

with an amine of formula $HNR^eR^f$, to obtain a compound of formula (I-a), wherein $R^7$ is $NR^eR^f$ and $R^1$ to $R^4$ are as defined hereinabove. This process is described in more detail with general scheme and procedure B.

In a certain embodiment, the compounds of formula (I-a) can be manufactured according to a process comprising reacting a compound of formula (I-b1):

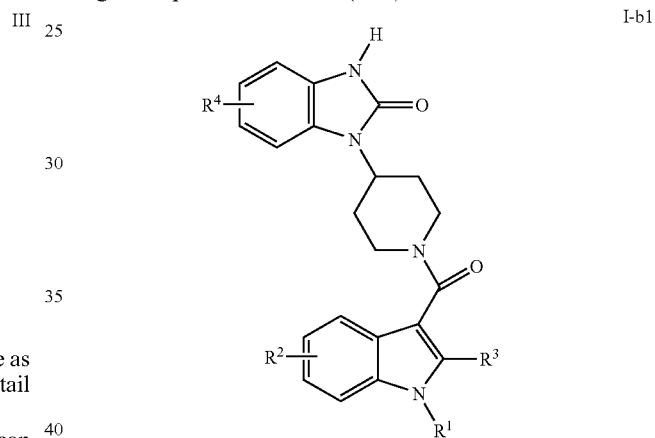

with $POCl_3$ to obtain a compound of formula (I-a), wherein $R^7$ is Cl and $R^1$ to $R^4$ are as defined hereinabove. This process is described in more detail with general scheme and procedure B.

In a certain embodiment, the compounds of formula (I-b) can be manufactured according to a process comprising reacting a compound of formula (I-b1):

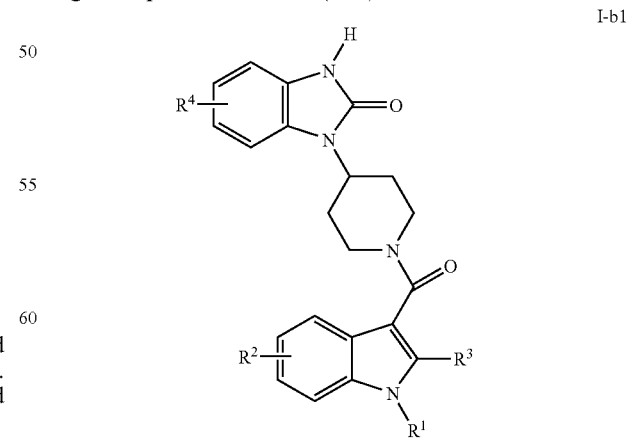

with a compound of formula $R^5$—X, to obtain a compound of formula (I-b), wherein $R^1$ and $R^5$ are different from H and wherein $R^2$ to $R^4$ are as defined hereinabove. This process is described in more detail with general scheme and procedure C.

The preparation of the compounds of the invention is hereafter described in more detail with general schemes A to D and corresponding general procedures.

General scheme and procedure A describe the most general route to prepare the compounds of formulae (I) and (IV), from which further compounds of formulae (I), (I-a) and (I-b) can be prepared with general schemes and procedures B, C and D.

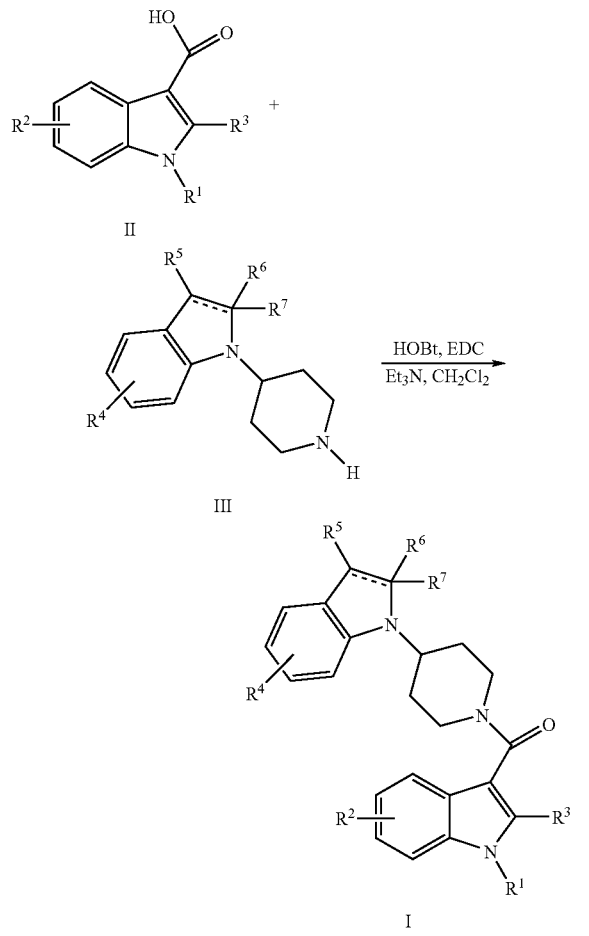

General Scheme A

To obtain compounds of the formula (I-b) in a certain embodiment of the invention, a starting material of formula III-b can be used in analogy to general scheme A, namely by reacting a compound of formula II with a compound of formula (III-b):

wherein $R^1$ to $R^5$ are as defined hereinabove.

Compounds of formula (I-b) can be prepared via an amide coupling between an indole 3-carboxylic acid of formula (II) and a piperidine derivative of formula (III). Indole 3-carboxylic acids of formula (II) are either commercially available or readily prepared using a procedure described in. *J. Med. Chem.* 1991, 34, 140, or prepared using a procedure described in the examples hereinafter. Alternatively, the compounds of formula (II) can be prepared following the general scheme D. The piperidine derivatives of formula (III) are either commercially available or prepared using conventional methods with commercially available starting material. An example of general procedure A is also given with general procedure I in the examples hereafter.

General Procedure B

Compounds of formula (I-a2) (compounds of formula (I-a) wherein $R^7$ is $NR^eR^f$) can be prepared by reaction of a chlorobenzimidazole derivative of formula (I-a1) (compounds of formula (I-a) wherein $R^7$ is Cl) with a substituted primary of secondary commercially available amine. Derivatives of formula (I-a1) are prepared by treatment of a compound of formula (I-b1) (compounds of formula (I-b) wherein $R^5$=H) with $POCl_3$ at high temperature (e.g under reflux).

General procedure B is further illustrated with the examples hereinafter.

General scheme C

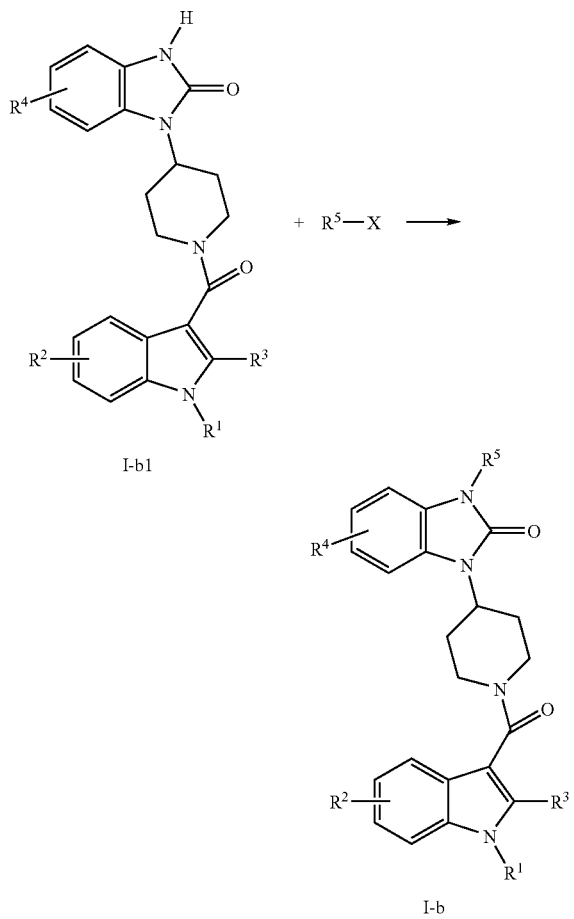

General Procedure C

General procedure C is suitable for the preparation of compounds of formula (I-b) wherein $R^1$ and $R^5$ are different from H. Such compounds can be prepared by the alkylation or arylation of a compound of formula (I-b1), wherein $R^1$ is not H, obtained according to general procedure A, with a commercially available electrophilic reactant $R^5$—X, wherein $R^5$ is $C_{1-6}$-alkyl or aryl, and X is halo. General procedure C is further illustrated with the examples hereinafter.

General scheme D

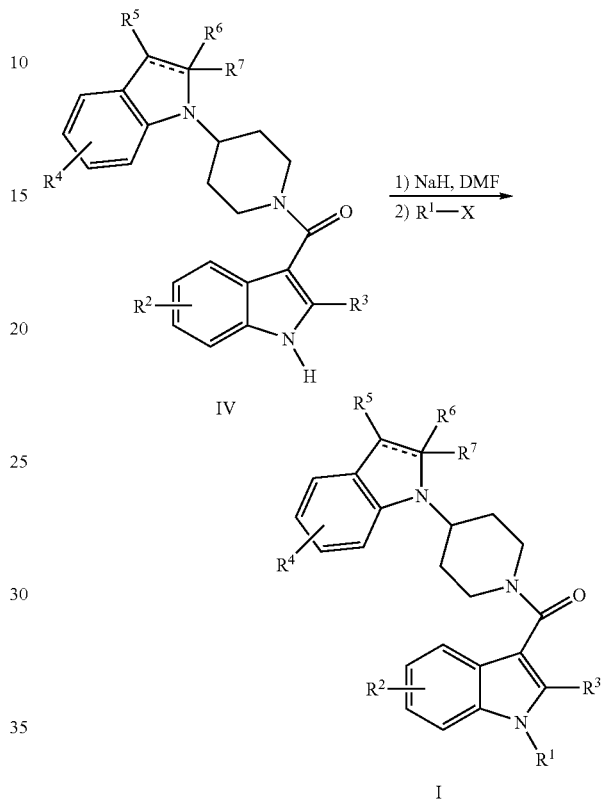

General Scheme D

Compounds of formula (I) with $R^1$ different from H can be prepared by N-deprotonation of an indole derivative (IV) (a compound of formula (I) wherein $R^1$ is H) followed by treatment with an electrophilic reactant $R^1$—X (wherein X is a leaving group, e.g. halo) which is either commercially available or easily prepared according to methods well known in the art and commercially available starting materials. Derivatives (IV) are prepared using the method described in the general schemes and procedures A, B and C. General scheme D is hereinafter further illustrated with general procedures II, III and IV.

General scheme E

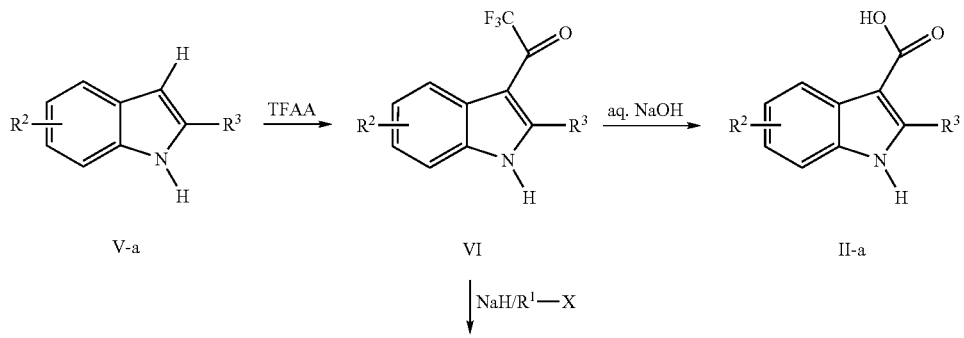

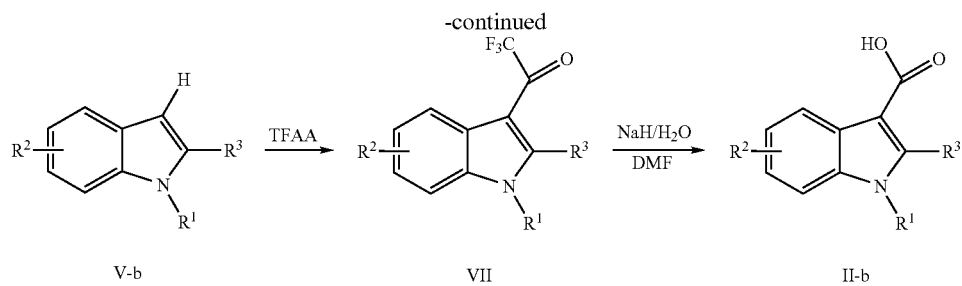

General Procedure E

The treatment of an indole derivative (V-a) with the trifluoroacetic anhydride in DMF affords intermediate (VI) which then can be hydrolyzed with an aqueous sodium hydroxide solution to give the 3-carboxylic acid indole derivative (II-a). Alternatively, (VI) can be reacted with an electrophilic reactant $R^1$—X to give (VII), which is then converted to the corresponding carboxylic acid derivative (II-b) with $NaH/H_2O$ in DMF (see *J. Org Chem.*, 1993, 10, 2862). Intermediate (VII) can alternatively be obtained by treatment of an indole derivative (V-b) with trifluoroacetic anhydride in a suitable solvent, e.g. DMF, dichloromethane or 1,2-dichloroethane. Addition of a suitable base may be advantageous.

General Procedure I: Amide Coupling

General procedure I is a particular embodiment of general procedure A. To a stirred solution of an indole-3-carboxylic acid derivative (1 mmol) in 10 ml $CH_2Cl_2$ was added (1.3 mmol) EDC, (1.3 mmol) HOBt, (1.3 mmol) $Et_3N$ and (1 mmol) of the amine derivative. The mixture was stirred overnight at RT and then poured onto water and extracted with $CH_2Cl_2$. The combined organic phases were dried over $Na_2SO_4$ and concentrated in vacuo. Flash chromatography or preparative HPLC afforded the title compound.

General Procedure II: Alkylation

To a stirred solution of 1-[1-(6-chloro-1H-indole-3-carbonyl)-piperidin-4-yl]-1,3-dihydro-benzoimidazol-2-one in DMF was added 2.1 eq. NaH (60% in oil). The mixture was stirred at RT for 30 min. before adding an electrophilic reactant $R^1$—X (1.1 eq.). The mixture was stirred an additional 14 hours at 60° C. and then poured onto water and extracted with ethyl acetate. The combined organic phases were dried over $Na_2SO_4$ and concentrated in vacuo. Purification by preparative HPLC afforded the corresponding derivatives.

General Procedure III: Acylation

A solution of the indole in dry DMF was treated with sodium hydride (1.05 eq) and stirred for 15 min at RT, then treated with the acid chloride (1.1 eq) and stirred at RT for 2 h. Purification by prep HPLC yielded the desired product.

General Procedure IV: Sulphonylation

A solution of the indole in dry DMF was treated with sodium hydride (1.05 eq) and stirred for 15 min at RT, then treated with the sulphonyl chloride (1.1 eq) and stirred at RT for 2 h. Purification by prep HPLC yielded the desired product.

Results

V1a Activity

Material & Method:

The human V1a receptor was cloned by RT-PCR from total human liver RNA. The coding sequence was subcloned in an expression vector after sequencing to confirm the identity of the amplified sequence. To demonstrate the affinity of the compounds from the present invention to the human V1a receptor binding studies were performed. Cell membranes were prepared from HEK293 cells transiently transfected with the expression vector and grown in 20 liter fermenters with the following protocol.

50 g of cells are resuspended in 30 ml freshly prepared ice cold Lysis buffer (50 mM HEPES, 1 mM EDTA, 10 mM MgCl2 adjusted to pH=7.4+ complete cocktail of protease inhibitor (Roche Diagnostics)). Homogenized with Polytron for 1 min and sonicated on ice for 2×2 minutes at 80% intensity (Vibracell sonicator). The preparation is centrifuged 20 min at 500 g at 4° C., the pellet is discarded, and the supernatant centrifuged 1 hour at 43,000 g at 4° C. (19,000 rpm). The pellet is resuspended in 12.5 ml Lysis buffer+12.5 ml Sucrose 20% and homogenized using a Polytron for 1-2 min. The protein concentration is determined by the Bradford method, and aliquots are stored at −80° C. until use. For binding studies 60 mg Yttrium silicate SPA beads (Amersham) are mixed with an aliquot of membrane in binding buffer (50 mM Tris, 120 mM NaCl, 5 mM, KCl, 2 mM CaCl2, 10 mM MgCl2) for 15 minutes with mixing. 50 ul of bead/membrane mixture is then added to each well of a 96 well plate, followed by 50 ul of 4 nM 3H-Vasopressin (American Radiolabeled Chemicals). For total binding measurement, 100 ul of binding buffer are added to the respective wells, for non-specific binding 100 ul of 8.4 mM cold vasopressin and for compound testing 100 ul of a serial dilution of each compound in 2% DMSO. The plate is incubated 1 h at room temperature, centrifuged 1 min at 1000 g and counted on a Packard Top-Count. Non-specific binding counts are subtracted from each well, and data is normalized to the maximum specific binding set at 100%. To calculate an IC 50, the curve is fitted using a non-linear regression model (XLfit), and the Ki is calculated using the Cheng-Prussoff equation.

| Compound of Example | Ki (nM) |
| --- | --- |
| 1 | 45 |
| 3 | 18 |
| 4 | 6 |
| 8 | 13 |
| 9 | 13 |
| 10 | 39 |
| 11 | 20 |
| 12 | 13 |
| 13 | 2 |
| 14 | 32 |
| 18 | 7 |
| 19 | 5 |
| 20 | 5 |
| 21 | 6 |
| 22 | 11 |

-continued

| Compound of Example | Ki (nM) |
|---|---|
| 23 | 6 |
| 24 | 2 |
| 25 | 20 |
| 26 | 0.7 |
| 27 | 5 |
| 28 | 12 |
| 29 | 22 |
| 30 | 35 |
| 31 | 25 |
| 33 | 15 |
| 34 | 9 |
| 35 | 5 |
| 36 | 6 |
| 37 | 15 |
| 38 | 2 |
| 39 | 18 |
| 40 | 13 |
| 41 | 14 |
| 42 | 18 |
| 43 | 62 |
| 44 | 17 |
| 45 | 43 |
| 46 | 2 |
| 47 | 5 |
| 48 | 3 |

The present invention also provides pharmaceutical compositions containing compounds of the invention, for example compounds of formula I and their pharmaceutically acceptable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are, however, usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts thereof and, if desired, one or more other therapeutically valuable substances into a galenical administration form together with one or more therapeutically inert carriers.

Compounds of formula (I) have good activity on the V1a receptor. Therefore, the invention further provides methods for treating dysmenorrhea, hypertension, chronic heart failure, inappropriate secretion of vasopressin, liver cirrhosis, nephrotic syndrome, obsessive compulsive disorder, anxiety and depressive disorders by administering a pharmaceutical composition comprising a therapeutically effective amount of a compound of formula I or a pharmaceutically acceptable salt thereof and a pharmaceutically acceptable carrier.

The dosage at which compounds of the invention can be administered can vary within wide limits and will, of course, be fitted to the individual requirements in each particular case. In general, in the case of oral administration a daily dosage of about 10 to 1000 mg per person of a compound of formula I should be appropriate, although the above upper limit can also be exceeded when necessary.

The following Examples illustrate the present invention without limiting it. All temperatures are given in degrees Celsius.

Example A

Tablets of the following composition are manufactured in the usual manner:

| | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

Example B

Capsules of the following composition are manufactured:

| | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatin capsules.

Example C

Suppositories of the following composition are manufactured:

| | mg/supp. |
|---|---|
| Active substance | 15 |
| Suppository mass | 1285 |
| Total | 1300 |

The suppository mass is melted in a glass or steel vessel, mixed thoroughly and cooled to 45° C.

Thereupon, the finely powdered active substance is added thereto and stirred until it has dispersed completely. The mixture is poured into suppository moulds of suitable size, left to cool; the suppositories are then removed from the moulds and packed individually in wax paper or metal foil.

Examples

General Procedure I

Amide Coupling

General procedure I is a particular embodiment of general procedure A. To a stirred solution of an indole-3-carboxylic acid derivative (1 mmol) in 10 ml $CH_2Cl_2$ was added (1.3 mmol) EDC, (1.3 mmol) HOBt, (1.3 mmol) $Et_3N$ and (1 mmol) of the amine derivative. The mixture was stirred overnight at RT and then poured onto water and extracted with $CH_2Cl_2$. The combined organic phases were dried over $Na_2SO_4$ and concentrated in vacuo. Flash chromatography or preparative HPLC afforded the title compound.

Where journal references are cited in the examples, the example was performed using the starting material listed with the reactants and conditions cited in the reference. All procedures in such references are well known to those of ordinary skill in the art. All journal references cited herein are incorporated by reference.

Examples of Compounds of Formula I-a

Example 1

(1-Benzyl-2-methyl-1H-indol-3-yl)-[4-(2-chloro-benzoimidazol-1-yl)-piperidin-1-yl]-methanone A mixture of 0.45 g (0.97 mmol) of 1-[1-(1-benzyl-2-methyl-1H-indole-3-carbonyl)-piperidin-4-yl]-1,3-dihydro-benzoimidazol-2-one (the preparation of which is described hereinafter) and phosphorus oxychloride (6 ml) was stirred at 100° C. for 2 hours and then allowed to cool. The reaction mixture was poured into ice-cold water, 10N NaOH was added until the ph=14, and the mixture was extracted with AcOEt. The combined organic phases were dried over $Na_2SO_4$ and concentrated in vacuo. R$^e$-crystallization in $Et_2O$ afforded 0.32 g (68%) of (1-benzyl-2-methyl-1H-indol-3-yl)-[4-(2-chloro-benzoimidazol-1-yl)-piperidin-1-yl]-methanone as white crystals. ES-MS m/e (%): 483.6 (M+H$^+$).

1-[1-(1-Benzyl-2-methyl-1H-indole-3-carbonyl)-piperidin-4-yl]-1,3-dihydro-benzoimidazol-2-one Amide coupling following the general procedure I:
Amine: 1-Piperidin-4-yl-1,3-dihydro-benzoimidazol-2-one (commercially available)
Acide: 1-Benzyl-2-methyl-1H-indole-3-carboxylic acid (the preparation of which is described hereinafter),
ES-MS m/e (%): 463.2 (M+H$^+$).

1-Benzyl-2-methyl-1H-indole-3-carboxylic acid

Using the procedure described in example 8 hereinafter, from 2-methyl-1H-indole-3-carboxylic acid (described in *J. Heterocyclic Chem.* 1977, 14, 1123) was prepared 1-benzyl-2-methyl-1H-indole-3-carboxylic acid.

Example 2

(1-Benzyl-2-methyl-1H-indol-3-yl)-{4-[2-(4-methyl-piperazin-1-yl)-benzoimidazol-1-yl]-piperidin-1-yl}-methanone A mixture of 20 mg (0.041 mmol) of (1-benzyl-2-methyl-1H-indol-3-yl)-[4-(2-chloro-benzoimidazol-1-yl)-piperidin-1-yl]-methanone (the preparation of which is described in example 1) and N-methyl-piperazine was heated in a sealed tube at 90° C. for 8 hours, cooled to RT and then concentrated in vacuo. Flash chromatography ($CH_2Cl_2$/MeOH 9/1) afforded 5 mg (22%) of (1-benzyl-2-methyl-1H-indol-3-yl)-{4-[2-(4-methyl-piperazin-1-yl)-benzoimidazol-1-yl]-piperidin-1-yl}-methanone as white solid. ES-MS m/e (%): 547.5 (M+H$^+$).

Example 3

(1-Benzyl-2-methyl-1H-indol-3-yl)-[4-(2-morpholin-4-yl-benzoimidazol-1-yl)-piperidin-1-yl]-methanone Using the same procedure described in example 2, from 30 mg (0.062 mmol) of (1-benzyl-2-methyl-1H-indol-3-yl)-[4-(2-chloro-benzoimidazol-1-yl)-piperidin-1-yl]-methanone (the preparation of which is described in example 1) and morpholine (0.5 ml) was prepared 20 mg (60%) of (1-benzyl-2-methyl-1H-indol-3-yl)-[4-(2-morpholin-4-yl-benzoimidazol-1-yl)-piperidin-1-yl]-methanone as light yellow solid. ES-MS m/e (%): 534.2 (M+H$^+$).

Example 4

(1-Benzyl-2-methyl-1H-indol-3-yl)-[4-(2-piperidin-1-yl-benzoimidazol-1-yl)-piperidin-1-yl]-methanone Using the same procedure described in example 2, from 30 mg (0.062 mmol) of (1-benzyl-2-methyl-1H-indol-3-yl)-[4-(2-chloro-benzoimidazol-1-yl)-piperidin-1-yl]-methanone (the preparation of which is described in example 1) and piperidine (0.5 ml) was prepared 18 mg (54%) of (1-benzyl-2-methyl-1H-indol-3-yl)-[4-(2-piperidin-1-yl-benzoimidazol-1-yl)-piperidin-1-yl]-methanone as light yellow solid. ES-MS m/e (%): 532.5 (M+H$^+$).

Example 5

[4-(2-Chloro-benzoimidazol-1-yl)-piperidin-1-yl]-(2-methyl-1H-indol-3-yl)-methanone Using the same procedure described in example 1, from 1.700 g (4.54 mmol) of 1-[1-(2-methyl-1H-indole-3-carbonyl)-piperidin-4-yl]-1,3-dihydro-benzoimidazol-2-one (the preparation of which is described in example 10) and phosphorus oxychloride (40 ml) was prepared 0.50 g (35%) of [4-(2-chloro-benzoimidazol-1-yl)-piperidin-1-yl]-(2-methyl-1H-indol-3-yl)-methanone as a light brown solid. ES-MS m/e (%): 393.2 (M+H$^+$).

Example 6

[4-(2-Dimethylamino-benzoimidazol-1-yl)-piperidin-1-yl]-(2-methyl-1H-indol-3-yl)-methanone Using the same procedure described in example 2, from 50 mg (0.127 mmol) of [4-(2-chloro-benzoimidazol-1-yl)-piperidin-1-yl]-(2-methyl-1H-indol-3-yl)-methanone (the preparation of which is described in example 5) and dimethyl amine (1.5 ml, 5.6M in EtOH) was prepared 42 mg (43%) of [4-(2-dimethylamino-benzoimidazol-1-yl)-piperidin-1-yl]-(2-methyl-1H-indol-3-yl)-methanone as light yellow solid. ES-MS m/e (%): 402.2 (M+H$^+$).

Example 7

[4-(2-Methylamino-benzoimidazol-1-yl)-piperidin-1-yl]-(2-methyl-1H-indol-3-yl)-methanone Using the same procedure described in example 2, from 50 mg (0.127 mmol) of [4-(2-chloro-benzoimidazol-1-yl)-piperidin-1-yl]-(2-methyl-1H-indol-3-yl)-methanone (the preparation of which is described in example 5) and methyl amine (1.5 ml, 8M in EtOH) was prepared 76 mg (78%) of [4-(2-methylamino-benzoimidazol-1-yl)-piperidin-1-yl]-(2-methyl-1H-indol-3-yl)-methanone as light yellow solid. ES-MS m/e (%): 388.1 (M+H$^+$).

Examples of Compounds of Formula I-b

Example 8

1-[1-(1-Benzyl-1H-indole-3-carbonyl)-piperidin-4-yl]-1,3-dihydro-benzoimidazol-2-one Amide coupling following the general procedure I:
Amine: 1-Piperidin-4-yl-1,3-dihydro-benzoimidazol-2-one (commercially available)
Acide: 1-Benzyl-1H-indole-3-carboxylic acid (the preparation of which is described hereinafter),
ES-MS m/e (%): 451.3 (M+H$^+$).

1-benzyl-1H-indole-3-carboxylic acid

To a stirred solution of 0.50 g (3.10 mmol) 1H-indole-3-carboxylic acid in 5 ml DMF was added 0.27 g (6.75 mmol) of NaH (60% in oil). The mixture was stirred at RT for 30 min. and then 0.39 ml (3.28 mmol) of benzyl bromide was added. The mixture was stirred an additional hour and then poured onto water and extracted with ethyl acetate. The combined organic phases were dried over $Na_2SO_4$ and concentrated in vacuo. Crystallization in $Et_2O$ afforded 0.61 g (78%) of 1-benzyl-1H-indole-3-carboxylic acid as a white solid. ES-MS m/e (%): 250 (M–H$^+$).

Example 9

1-{1-[(1-benzyl-2-methyl-1H-indol-3-yl)carbonyl]piperidin-4-yl}-3-methyl-1,3-dihydro-2H-benzimidazol-2-one Amide coupling following the general procedure I:
Amine: 1-Methyl-3-piperidin-4-yl-1,3-dihydro-benzoimidazol-2-one (described in WO0214315),
Acide: 1-Benzyl-2-methyl-1H-indole-3-carboxylic acid (described in example 1),
ES-MS m/e (%): 479.4 (M+H$^+$).

Example 10

1-[1-(2-Methyl-1H-indole-3-carbonyl)-piperidin-4-yl]-1,3-dihydro-benzoimidazol-2-one Amide coupling following the general procedure I:
Amine: 1-Piperidin-4-yl-1,3-dihydro-benzoimidazol-2-one (commercially available),
Acide: 2-Methyl-1H-indole-3-carboxylic acid (described in *J. Heterocyclic Chem.* 1977, 14, 1123),
ES-MS m/e (%): 375.2 (M+H$^+$).

Example 11

1-[1-(1-Isopropyl-6-methoxy-1H-indole-3-carbonyl)-piperidin-4-yl]-1,3-dihydro-benzoimidazol-2-one Amide coupling following the general procedure I:
Amine: 1-Piperidin-4-yl-1,3-dihydro-benzoimidazol-2-one (commercially available),
Acide: 1-Isopropyl-6-methoxy-1H-indole-3-carboxylic acid (described in US20040067939),
ES-MS m/e (%): 433.6 (M+H$^+$).

Example 12

1-[1-(6-Fluoro-1-isopropyl-1H-indole-3-carbonyl)-piperidin-4-yl]-1,3-dihydro-benzoimidazol-2-one Amide coupling following the general procedure I:
Amine: 1-Piperidin-4-yl-1,3-dihydro-benzoimidazol-2-one (commercially available),
Acide: 6-Fluoro-1-isopropyl-1H-indole-3-carboxylic acid (described in US20040067939),
ES-MS m/e (%): 421.5 (M+H$^+$).

Example 13

1-[1-(6-Chloro-1-isopropyl-1H-indole-3-carbonyl)-piperidin-4-yl]-1,3-dihydro-benzoimidazol-2-one Amide coupling following the general procedure I:
Amine: 1-Piperidin-4-yl-1,3-dihydro-benzoimidazol-2-one (commercially available),
Acide: 6-Chloro-1-isopropyl-1H-indole-3-carboxylic acid (described in US20040067939),
ES-MS m/e (%): 437.5 (M+H$^+$).

Example 14

1-[1-(1-Isopropyl-1H-indole-3-carbonyl)-piperidin-4-yl]-1,3-dihydro-benzoimidazol-2-one Amide coupling following the general procedure I:
Amine: 1-Piperidin-4-yl-1,3-dihydro-benzoimidazol-2-one (commercially available),
Acide: 1-Isopropyl-1H-indole-3-carboxylic acid (described in *J. Med. Chem.* 1994, 37, 2090),
ES-MS m/e (%): 403.5 (M+H$^+$).

Example 15

1-[1-(1-Methyl-1H-indole-3-carbonyl)-piperidin-4-yl]-1,3-dihydro-benzoimidazol-2-one Amide coupling following the general procedure I:
Amine: 1-Piperidin-4-yl-1,3-dihydro-benzoimidazol-2-one (commercially available),
Acide: 1-Methyl-1H-indole-3-carboxylic acid (commercially available),
ES-MS m/e (%): 375.5 (M+H$^+$).

Example 16

1-[1-(1H-Indole-3-carbonyl)-piperidin-4-yl]-1,3-dihydro-benzoimidazol-2-one

Amide coupling following the general procedure I:
Amine: 1-Piperidin-4-yl-1,3-dihydro-benzoimidazol-2-one (commercially available),
Acide: 1H-Indole-3-carboxylic acid (commercially available),
ES-MS m/e (%): 361.2 (M+H$^+$).

Example 17

1-{1-[2-(Pyrrolidine-1-carbonyl)-1H-indole-3-carbonyl]-piperidin-4-yl}-1,3-dihydro-benzoimidazol-2-one Amide coupling following the general procedure I:
Amine: 1-Piperidin-4-yl-1,3-dihydro-benzoimidazol-2-one (commercially available), Acide: 2-(pyrrolidine-1-carbonyl)-1H-indole-3-carboxylic acid (the preparation is described hereinafter).
ES-MS m/e (%): 456.4 (M+H$^+$).

a) (1H-indol-2-yl)-pyrrolidin-1-yl-methanone

To a stirred solution of 0.300 g (1.86 mmol) of 1H-indole-2-carboxylic acid in CH$_2$Cl$_2$ (10 ml) was added 0.428 g (2.23 mmol) of EDC, 0.302 g (2.23 mmol) of HOBt, 0.28 ml (2.04 mmol) of Et$_3$N and 0.17 ml (2.04 mmol) of pyrrolidine. The reaction mixture was stirred at RT over the night and then poured onto water and extracted with CH$_2$Cl$_2$. The combined organic phases were dried over Na$_2$SO$_4$ and concentrated in vacuo. R$^e$-crystallization in Et$_2$O afforded 0.31 g (78%) of (1H-indol-2-yl)-pyrrolidin-1-yl-methanone as white crystals.

b) 2-(pyrrolidine-1-carbonyl)-1H-indole-3-carboxylic acid

Using a procedure described in *J. Med. Chem.* 1991, 34, 140, from 100 mg (0.46 mmol) of (1H-indol-2-yl)-pyrrolidin-1-yl-methanone was prepared 28 mg (23%) of 2-(pyrrolidine-1-carbonyl)-1H-indole-3-carboxylic acid as a light brown solid. ES-MS m/e (%): 257 (M–H$^+$).

Example 18

1-[1-(6-Chloro-1H-indole-3-carbonyl)-piperidin-4-yl]-1,3-dihydro-benzoimidazol-2-one Amide coupling following the general procedure I:
Amine: 1-Piperidin-4-yl-1,3-dihydro-benzoimidazol-2-one (commercially available),
Acide: 6-chloro-1H-indole-3-carboxylic acid (described hereinafter)
ES-MS m/e (%): 395.4 (M+H$^+$).

6-chloro-1H-indole-3-carboxylic acid

Using a procedure described in *J. Med. Chem.* 1991, 34, 140, from 7.0 g (0.046 mmol) of 6-chloro-1H-indole was prepared 5.80 g (64%) of 6-chloro-1H-indole-3-carboxylic acid as a light brown solid. ES-MS m/e (%): 194 (M–H$^+$).

Example 19

1-[1-(6-Chloro-5-fluoro-1H-indole-3-carbonyl)-piperidin-4-yl]-1,3-dihydro-benzoimidazol-2-one Amide coupling following the general procedure I:
Amine: 1-Piperidin-4-yl-1,3-dihydro-benzoimidazol-2-one (commercially available),
Acide: 6-chloro-5-fluoro-1H-indole-3-carboxylic acid (the preparation of which is described hereinafter),
ES-MS m/e (%): 413.2 (M+H$^+$).

a) 6-chloro-5-fluoro-1H-indole

Following the procedure described in WO9747598, from 6-chloro-5-fluoro-1H-indole-2,3-dione was prepared 6-chloro-5-fluoro-1H-indole.

b) 6-chloro-5-fluoro-1H-indole-3-carboxylic acid

Following a procedure described in *J. Med. Chem.* 1991, 34, 140, from 0.25 g (1.47 mmol) of 6-chloro-5-fluoro-1H-indole was prepared 0.35 g (90%) of 6-chloro-5-fluoro-1H-indole-3-carboxylic acid as a light brown solid. ES-MS m/e (%): 213 (M–H$^+$).

Example 20

1-[1-(1-Benzyl-2-methyl-1H-indole-3-carbonyl)-piperidin-4-yl]-3-(2-dimethylamino-ethyl)-1,3-dihydro-benzoimidazol-2-one To a stirred solution of 20 mg (0.043 mmol) of 1-[1-(1-benzyl-2-methyl-1H-indole-3-carbonyl)-piperidin-4-yl]-1,3-dihydro-benzoimidazol-2-one (the preparation of which is described hereinafter) in DMF (3 ml) at RT, was added 2.0 mg (0.051 mmol) of NaH (60% in oil). The mixture was stirred 20 min. and then 5.6 mg (0.051 mmol) of (2-chloro-ethyl)-dimethyl-amine in 1 ml of DMF was added. The mixture was stirred an additional 5 hours at 50° C. and then poured onto water and extracted with ethyl acetate. The combined organic phases were dried over Na$_2$SO$_4$ and concentrated in vacuo. Flash chromatography (CH$_2$Cl$_2$/MeOH 8/2) afforded 12 mg (50%) of 1-[1-(1-benzyl-2-methyl-1H-indole-3-carbonyl)-piperidin-4-yl]-3-(2-dimethylamino-ethyl)-1,3-dihydro-benzoimidazol-2-one as a viscous oil. ES-MS m/e (%): 536.2 (M+H$^+$).

1-[1-(1-Benzyl-2-methyl-1H-indole-3-carbonyl)-piperidin-4-yl]-1,3-dihydro-benzoimidazol-2-one Amide coupling following the general procedure I:
Amine: 1-Piperidin-4-yl-1,3-dihydro-benzoimidazol-2-one (commercially available),
Acide: 1-Benzyl-2-methyl-1H-indole-3-carboxylic acid (described in example 1),
ES-MS m/e (%): 463.2 (M+H$^+$).

Example 21

{6-Chloro-3-[4-(2-oxo-2,3-dihydro-benzoimidazol-1-yl)-piperidine-1-carbonyl]-indol-1-yl}-acetonitrile To a stirred solution of 40 mg (0.101 mmol) of 1-[1-(6-Chloro-1H-indole-3-carbonyl)-piperidin-4-yl]-1,3-dihydro-benzoimidazol-2-one (the preparation of which has been described in example 18) in 5 ml DMF was added 4.2 mg (0.105 mmol) NaH (60% in oil). The mixture was stirred at RT for 30 min. and then 8.3 mg (0.11 mmol) of chloroacetonitrile was added. The mixture was stirred an additional hour and then poured onto water and extracted with ethyl acetate. The combined organic phases were dried over Na$_2$SO$_4$ and concentrated in vacuo. Preparative HPLC afforded 6 mg (14%) of {6-Chloro-3-[4-(2-oxo-2,3-dihydro-benzoimidazol-1-yl)-piperidine-1-carbonyl]-indol-1-yl}-acetonitrile as a white solid.
ES-MS m/e (%): 434 (M+H$^+$).

Example 22

1-{1-[2-(2-Methyl-butyryl)-1H-indole-3-carbonyl]-piperidin-4-yl}-1,3-dihydro-benzoimidazol-2-one Amide coupling following the general procedure I:
Amine: 1-Piperidin-4-yl-1,3-dihydro-benzoimidazol-2-one (commercially available),
Acide: 2-(2-Methyl-butyryl)-1H-indole-3-carboxylic acid (commercially available)
ES-MS m/e (%): 445 (M+H$^+$).

Example 23

1-[1-(1-Benzyl-2-methyl-1H-indole-3-carbonyl)-piperidin-4-yl]-1,3-dihydro-benzoimidazol-2-one Amide coupling following the general procedure I:
Amine: 1-Piperidin-4-yl-1,3-dihydro-benzoimidazol-2-one (commercially available),
Acid: 1-Benzyl-2-methyl-1H-indole-3-carboxylic acid (described herein above),
ES-MS m/e (%): 463.0 (M−H+).

Example 24

1-[1-(1-Benzyl-6-chloro-1H-indole-3-carbonyl)-piperidin-4-yl]-1,3-dihydro-benzoimidazol-2-one a) 6-Chloro-1H-indole-3-carboxylic acid Using a procedure described in *J. Med. Chem.* 1991, 34, 140, from 7.0 g (0.046 mmol) of 6-chloro-1H-indole were prepared 5.80 g (64%) of 6-chloro-1H-indole-3-carboxylic acid as a light brown solid.
ES-MS m/e (%): 194 (M−H+).

b) 6-Chloro-1H-indole-3-carboxylic acid methyl ester 1 g of 6-chloro-1H-indole-3-carboxylic acid were heated at reflux in MeOH with 3 drop of concentrated $H_2SO_4$ overnight. Concentration in vacuo afforded the title compound in quantitative yield.

c) 6-Chloro-1-(2-dimethylamino-ethyl)-1H-indole-3-carboxylic acid

To a stirred solution of 80 mg (0.38 mol) of 6-chloro-1H-indole-3-carboxylic acid methyl ester in 5 ml of DMF were added 50 mg of NaH (3 eq, 55H in oil) at RT. After 20 min, 66 mg (0.45 mmol, 1.2 eq.) of (2-chloro-ethyl)-dimethyl-amine hydrochloride were added and stirring was continued overnight at 60° C. Extraction with EtOAc/aq. $NH_4Cl$ followed by flash chromatography yielded 45 mg of crude 6-chloro-1-(2-dimethylamino-ethyl)-1H-indole-3-carboxylic acid methyl ester.
The ester was hydrolyzed in a mixture of $H_2O$/THF/MeOH (ratio 1:1:1) with $LiOH.H_2O$ (3 eq.). The reaction mixture was stirred at 40° C. overnight. The acid was extracted several times with EtOAc, and the combined organic phases were dried over $Na_2SO_4$. Recrystallisation in $Et_2O$ afforded 35 mg (34% overall yield) of the title compound as a white solid.
ES-MS m/e (%): 265.8 (M−H+).

d) 1-[1-(1-Benzyl-6-chloro-1H-indole-3-carbonyl)-piperidin-4-yl]-1,3-dihydro-benzoimidazol-2-one Following general procedure I, the coupling of (commercially available) 1-piperidin-4-yl-1,3-dihydro-benzoimidazol-2-one with 1-benzyl-6-chloro-1H-indole-3-carboxylic acid gave the title compound.
ES-MS m/e (%): 485.5 (M+H+).

Example 25

1-[1-(1-Cyclohexylmethyl-1H-indole-3-carbonyl)-piperidin-4-yl]-1,3-dihydro-benzoimidazol-2-one Following general procedure I, the coupling of (commercially available) 1-piperidin-4-yl-1,3-dihydro-benzoimidazol-2-one with 1-cyclohexylmethyl-1H-indole-3-carboxylic acid (described in Bioorganic & Medicinal Chemistry Letters (2005), 15(11), 2734-2737) gave the title compound.
ES-MS m/e (%): 457.6 (M+H+).

Example 26

1-{1-[6-Chloro-1-(2-dimethylamino-ethyl)-1H-indole-3-carbonyl]-piperidin-4-yl}-1,3-dihydro-benzoimidazol-2-one Amide coupling following the general procedure I:
Amine: 1-Piperidin-4-yl-1,3-dihydro-benzoimidazol-2-one (commercially available),
Acid: 6-Chloro-1-(2-dimethylamino-ethyl)-1H-indole-3-carboxylic acid (described herein after),
ES-MS m/e (%): 466.0 (M−H+).

Example 27

1-[1-(6-Chloro-1H-indole-3-carbonyl)-piperidin-4-yl]-3-(2-dimethylamino-ethyl)-1,3-dihydro-benzoimidazol-2-one a) 4-(2-Oxo-2,3-dihydro-benzoimidazol-1-yl)-piperidine-1-carboxylic acid tert-butyl ester To a stirred solution of 300 mg (1.4 mmol) of 1-piperidin-4-yl-1,3-dihydro-benzoimidazol-2-one (commercially available) in 15 ml of $CH_2Cl_2$ were added 34 mg (0.28 mmol, 0.2 eq.) of DMAP, 190 μl (1.4 mmol, 1 eq.) of $Et_3N$ and 301 mg (1.4 mmol, 1 eq.) of $(BOC)_2O$. After stirring at RT overnight the reaction mixture was poured on water and extracted with $CH_2Cl_2$. Column chromatography ($SiO_2$, EtOAc/Hept. 1:1) afforded 360 mg (82%) of the title compound as a white solid.

b) 1-(2-Dimethylamino-ethyl)-3-piperidin-4-yl-1,3-dihydro-benzoimidazol-2-one

To a solution of 320 mg (1 mmol) of 4-(2-oxo-2,3-dihydro-benzoimidazol-1-yl)-piperidine-1-carboxylic acid tert-butyl ester in 5 ml of DMF were added 218 mg (1.5 mmol, 1.5 eq.) of (2-chloro-ethyl)-dimethyl-amine hydrochloride and 418 mg (3 mmol, 3 eq.) of $K_2CO_3$. Stirring was continued at 60° C. over night. The mixture was poured on water and the product extracted with EtOAc. The organic phases were dried over $Na_2SO_4$ and concentration in vacuo afforded crude 4-[3-(2-dimethylamino-ethyl)-2-oxo-2,3-dihydro-benzoimidazol-1-yl]-piperidine-1-carboxylic acid tert-butyl ester as an off-white solid. This crude material was then dissolved in 5 ml of $CH_2Cl_2$ and 1 ml of TFA was added. After 2 hours at RT, the reaction was quenched by addition of aq. $NaHCO_3$ (pH=9), and the product extracted with $CH_2Cl_2$. Concentration in vacuo afforded 200 mg (61%) of the title compound as a white solid.
ES-MS m/e (%): 289.3 (M+H+).

c) 1-[1-(6-Chloro-1H-indole-3-carbonyl)-piperidin-4-yl]-3-(2-dimethylamino-ethyl)-1,3-dihydro-benzoimidazol-2-one Amide coupling following the general procedure I:
Amine: 1-(2-Dimethylamino-ethyl)-3-piperidin-4-yl-1,3-dihydro-benzoimidazol-2-one,
Acid: 6-Chloro-1H-indole-3-carboxylic acid.
ES-MS m/e (%): 466.0 (M+H+).

Example 28

1-{1-[6-Chloro-1-(3-fluoro-benzoyl)-1H-indole-3-carbonyl]-piperidin-4-yl}-1,3-dihydro-benzoimidazol-2-one Following general procedure III, the acylation of 1-[1-(6-chloro-1H-indole-3-carbonyl)-piperidin-4-yl]-1,3-dihydro-benzoimidazol-2-one with commercially available 3-fluoro-benzoyl chloride gave the title compound.
ES-MS m/e (%): 517.4 (M+H$^+$).

Example 29

1-(1-{6-Chloro-1-[2-(3-fluoro-phenyl)-2-oxo-ethyl]-1H-indole-3-carbonyl}-piperidin-4-yl)-1,3-dihydro-benzoimidazol-2-one Following general procedure II, the alkylation of 1-[1-(6-chloro-1H-indole-3-carbonyl)-piperidin-4-yl]-1,3-dihydro-benzoimidazol-2-one with commercially available 2-bromo-1-(3-fluoro-phenyl)-ethanone gave the title compound.
ES-MS m/e (%): 531.3 (M+H$^+$).

Example 30

1-{1-[6-Chloro-1-(2-fluoro-benzoyl)-1H-indole-3-carbonyl]-piperidin-4-yl}-1,3-dihydro-benzoimidazol-2-one Following general procedure III, the acylation of 1-[1-(6-chloro-1H-indole-3-carbonyl)-piperidin-4-yl]-1,3-dihydro-benzoimidazol-2-one with commercially available 2-fluoro-benzoyl chloride gave the title compound.
ES-MS m/e (%): 517.4 (M+H$^+$).

Example 31

1-{1-[6-Chloro-1-(2,3-difluoro-benzoyl)-1H-indole-3-carbonyl]-piperidin-4-yl}-1,3-dihydro-benzoimidazol-2-one Following general procedure III, the acylation of 1-[1-(6-chloro-1H-indole-3-carbonyl)-piperidin-4-yl]-1,3-dihydro-benzoimidazol-2-one with commercially available 2,3-difluoro-benzoyl chloride gave the title compound.
ES-MS m/e (%): 535.4 (M+H$^+$).

Example 32

1-{1-[6-Chloro-1-(3,5-difluoro-benzenesulfonyl)-1H-indole-3-carbonyl]-piperidin-4-yl}-1,3-dihydro-benzoimidazol-2-one Following general procedure IV, the sulphonylation of 1-[1-(6-chloro-1H-indole-3-carbonyl)-piperidin-4-yl]-1,3-dihydro-benzoimidazol-2-one with commercially available 3,5-difluoro-benzenesulfonyl chloride gave the title compound.
ES-MS m/e (%): 571.4 (M+H$^+$).

Example 33

1-{1-[6-Chloro-1-(3,5-difluoro-benzyl)-1H-indole-3-carbonyl]-piperidin-4-yl}-1,3-dihydro-benzoimidazol-2-one Following general procedure II, the alkylation of 1-[1-(6-chloro-1H-indole-3-carbonyl)-piperidin-4-yl]-1,3-dihydro-benzoimidazol-2-one with commercially available 1-chloromethyl-3,5-difluoro-benzene gave the title compound.
ES-MS m/e (%): 521.4 (M+H$^+$).

Example 34

1-{1-[6-Chloro-1-(3-fluoro-benzyl)-1H-indole-3-carbonyl]-piperidin-4-yl}-1,3-dihydro-benzoimidazol-2-one Following general procedure II, the alkylation of 1-[1-(6-chloro-1H-indole-3-carbonyl)-piperidin-4-yl]-1,3-dihydro-benzoimidazol-2-one with commercially available 1-chloromethyl-3-fluoro-benzene gave the title compound.
ES-MS m/e (%): 503.4 (M+H$^+$).

Example 35

1-(1-{6-Chloro-1-[2-(2,5-difluoro-phenyl)-2-oxo-ethyl]-1H-indole-3-carbonyl}-piperidin-4-yl)-1,3-dihydro-benzoimidazol-2-one Following general procedure II, the alkylation of 1-[1-(6-chloro-1H-indole-3-carbonyl)-piperidin-4-yl]-1,3-dihydro-benzoimidazol-2-one with commercially available 2-chloro-1-(2,5-difluoro-phenyl)-ethanone gave the title compound.
ES-MS m/e (%): 549.4 (M+H$^+$).

Example 36

1-(1-{6-Chloro-1-[2-(2,4-difluoro-phenyl)-2-oxo-ethyl]-1H-indole-3-carbonyl}-piperidin-4-yl)-1,3-dihydro-benzoimidazol-2-one Following general procedure II, the alkylation of 1-[1-(6-chloro-1H-indole-3-carbonyl)-piperidin-4-yl]-1,3-dihydro-benzoimidazol-2-one with commercially available 2-chloro-1-(2,4-difluoro-phenyl)-ethanone gave the title compound.
ES-MS m/e (%): 549.4 (M+H$^+$).

Example 37

1-{1-[6-Chloro-1-(3,5-difluoro-benzoyl)-1H-indole-3-carbonyl]-piperidin-4-yl}-1,3-dihydro-benzoimidazol-2-one Following general procedure III, the acylation of 1-[1-(6-chloro-1H-indole-3-carbonyl)-piperidin-4-yl]-1,3-dihydro-benzoimidazol-2-one with commercially available 3,5-difluoro-benzoyl chloride gave the title compound.
ES-MS m/e (%): 535.4 (M+H$^+$).

Example 38

1-(1-{6-Chloro-1-[2-(2-fluoro-phenyl)-2-oxo-ethyl]-1H-indole-3-carbonyl}-piperidin-4-yl)-1,3-dihydro-benzoimidazol-2-one Following general procedure II, the alkylation of 1-[1-(6-chloro-1H-indole-3-carbonyl)-piperidin-4-yl]-1,3-dihydro-benzoimidazol-2-one with commercially available 2-chloro-1-(2-fluoro-phenyl)-ethanone gave the title compound.
ES-MS m/e (%): 531.4 (M+H$^+$).

Example 39

1-(1-{6-Chloro-1-[2-(3,4-difluoro-phenyl)-2-oxo-ethyl]-1H-indole-3-carbonyl}-piperidin-4-yl)-1,3-dihydro-benzoimidazol-2-one Following general procedure II, the alkylation of 1-[1-(6-chloro-1H-indole-3-carbonyl)-piperidin-4-yl]-1,3-dihydro-benzoimidazol-2-one with commercially available 2-chloro-1-(3,4-difluoro-phenyl)-ethanone gave the title compound.
ES-MS m/e (%): 549.4 (M+H$^+$).

Example 40

1-{1-[6-Chloro-1-(3,5-difluoro-phenyl)-1H-indole-3-carbonyl]-piperidin-4-yl}-1,3-dihydro-benzoimidazol-2-one a) 1-[6-Chloro-1-(3,5-difluoro-phenyl)-1H-indol-3-yl]-2,2,2-trifluoro-ethanone To a solution of 1-(6-chloro-1H-indol-3-yl)-2,2,2-trifluoro-ethanone (described in US 2004067939) in $CH_2Cl_2$ (in the presence of 0.4 nM molecular sieve) were added anhydrous $Cu(OAc)_2$ (2 eq.), 3,5-difluorophenylboronic acid (3 eq.) and pyridine (4 eq.). The reaction mixture was stirred at RT for 16 h under an air atmosphere, filtered over decalite, washed with $CH_2Cl_2$ and concentrated in vacuo. Chromatography (hexane/EtOAc: 9:1) gave the title compound in 71% yield.

ES-MS m/e (%): 360.0 (M+H$^+$).

b) 6-Chloro-1-(3,5-difluoro-phenyl)-1H-indole-3-carboxylic acid

A suspension of 1-[6-chloro-1-(3,5-difluoro-phenyl)-1H-indol-3-yl]-2,2,2-trifluoro-ethanone in 3N aqueous NaOH was stirred at 70° C. for 48 h. After washing with $CH_2Cl_2$, the aqueous phase was acidified to pH 1 and extracted with $CH_2Cl_2$. Concentration in vacuo gave the title compound in 70% yield.

ES-MS m/e (%): 306.0 (M−H$^+$).

c) 1-{1-[6-Chloro-1-(3,5-difluoro-phenyl)-1H-indole-3-carbonyl]-piperidin-4-yl}-1,3-dihydro-benzoimidazol-2-one Following general procedure I, the coupling of (commercially available) 1-piperidin-4-yl-1,3-dihydro-benzoimidazol-2-one with 6-chloro-1-(3,5-difluoro-phenyl)-1H-indole-3-carboxylic acid gave the title compound.

ES-MS m/e (%): 507.0 (M+H$^+$).

Example 41

1-{1-[6-Chloro-1-(piperidine-1-carbonyl)-1H-indole-3-carbonyl]-piperidin-4-yl}-1,3-dihydro-benzoimidazol-2-one To a stirred solution of 30 mg of 1-[1-(6-chloro-1H-indole-3-carbonyl)-piperidin-4-yl]-1,3-dihydro-benzoimidazol-2-one in 1 ml of DMF were added 1.1 eq. of NaH (55% in oil). The reaction mixture was stirred for 30 min. before the addition of 1.2 eq. of piperidine-1-carbonyl chloride. The crude reaction mixture was purified by preparative HPLC to afforded 21 mg of the title compound as a yellow powder.

ES-MS m/e (%): 506.4 (M+H$^+$).

Example 42

1-{1-[6-Chloro-1-(2-oxo-2-piperidin-1-yl-ethyl)-1H-indole-3-carbonyl]-piperidin-4-yl}-3-(2-oxo-2-piperidin-1-yl-ethyl)-1,3-dihydro-benzoimidazol-2-one To a stirred solution of 30 mg of 1-[1-(6-chloro-1H-indole-3-carbonyl)-piperidin-4-yl]-1,3-dihydro-benzoimidazol-2-one in 1 ml of DMF were added 1.1 eq. of NaH (55% in oil). The reaction mixture was stirred for 30 min. before the addition of 1.2 eq. of 2-chloro-1-piperidin-1-yl-ethanone. The crude reaction mixture was directly purified by preparative HPLC to afforded 4 mg of the title compound as a white powder.

ES-MS m/e (%): 645.0 (M+H$^+$).

Example 43

2-{6-Chloro-3-[4-(3-diethylcarbamoylmethyl-2-oxo-2,3-dihydro-benzoimidazol-1-yl)-piperidine-1-carbonyl]-indol-1-yl}-N,N-diethyl-acetamide To a stirred solution of 30 mg of 1-[1-(6-chloro-1H-indole-3-carbonyl)-piperidin-4-yl]-1,3-dihydro-benzoimidazol-2-one in 1 ml of DMF were added 1.1 eq. of NaH (55% in oil). The reaction mixture was stirred for 30 min. before the addition of 1.2 eq. of 2-chloro-N,N-diethyl-acetamide. The crude reaction mixture was purified by preparative HPLC to afforded 6 mg of the title compound as a white powder.

ES-MS m/e (%): 621.0 (M+H$^+$).

Example 44

1-(1-{6-Chloro-1-[2-(3,5-difluoro-phenyl)-2-oxo-ethyl]-1H-indole-3-carbonyl}-piperidin-4-yl)-1,3-dihydro-benzoimidazol-2-one Following general procedure II, the alkylation of 1-[1-(6-chloro-1H-indole-3-carbonyl)-piperidin-4-yl]-1,3-dihydro-benzoimidazol-2-one, with commercially available 2-chloro-1-(3,5-difluoro-phenyl)-ethanone gave the title compound.

ES-MS m/e (%): 549.4 (M+H$^+$).

Example 45

1-(1-{6-Chloro-1-[2-(5-methyl-2-phenyl-oxazol-4-yl)-2-oxo-ethyl]-1H-indole-3-carbonyl}-piperidin-4-yl)-1,3-dihydro-benzoimidazol-2-one Following general procedure II, the alkylation of 1-[1-(6-chloro-1H-indole-3-carbonyl)-piperidin-4-yl]-1,3-dihydro-benzoimidazol-2-one, 2-bromo-1-(5-methyl-2-phenyl-oxazol-4-yl)-ethanone (described in Journal of Medicinal Chemistry (1992), 35(14), 2617-26) gave the title compound.

ES-MS m/e (%): 594.4 (M+H$^+$).

Example 46

2-{6-Chloro-3-[4-(2-oxo-2,3-dihydro-benzoimidazol-1-yl)-piperidine-1-carbonyl]-indol-1-yl}-N,N-dimethyl-acetamide To a stirred solution of 30 mg of 1-[1-(6-chloro-1H-indole-3-carbonyl)-piperidin-4-yl]-1,3-dihydro-benzoimidazol-2-one in 1 ml of DMF were added 1.1 eq. of NaH (55% in oil). The reaction mixture was stirred for 30 min. before the addition of 1.2 eq. of 2-chloro-N,N-dimethyl-acetamide. The crude reaction mixture was purified by preparative HPLC to afforded 10 mg of the title compound as a white powder.

ES-MS m/e (%): 480.5 (M+H$^+$).

Example 47

2-{6-Chloro-5-methyl-3-[4-(2-oxo-2,3-dihydro-benzoimidazol-1-yl)-piperidine-1-carbonyl]-indol-1-yl}-N,N-dimethyl-acetamide a) 1-(6-Chloro-5methyl-1H-indol-3-yl)-2,2,2-trifluoro-ethanone

Using a procedure described in J. Med. Chem. 1991, 34, 140, from 0.250 g (0.002 mol) of 6-chloro-5-methyl-1H-indole were prepared 0.38 g (96%) of the title compound as a white solid.

b) 2-[6-Chloro-5-methyl-3-(2,2,2-trifluoro-acetyl)-indol-1-yl]-N,N-dimethyl-acetamide To a stirred solution of 1-(6-chloro-5methyl-1H-indol-3-yl)-2,2,2-trifluoro-ethanone (0.38 g) in 10 ml of DMF at 0° C., were added 64 mg (1.1 eq.) of NaH (60% in oil). The mixture was stirred for 30 min. before 0.16 ml (1.1 eq.) of dimethylamino-acetyl chloride were added. The mixture was stirred an additional hour and then poured onto water and extracted with ethyl acetate. The combined organic phases were dried over $Na_2SO_4$ and concentrated in vacuo to afford 300 mg (60%) of the title compound as a white solid.

c) 6-Chloro-1-dimethylcarbamoylmethyl-5-methyl-1H-indole-3-carboxylic acid

Using a procedure similar to that described in *J. Med. Chem.* 1991, 34, 140, from 0.280 g of 2-[6-chloro-5-methyl-3-(2,2,2-trifluoro-acetyl)-indol-1-yl]-N,N-dimethyl-acetamide were prepared 0.18 g (76%) of the title compound as a white solid.

d) 2-{6-Chloro-5-methyl-3-[4-(2-oxo-2,3-dihydro-benzoimidazol-1-yl)-piperidine-1-carbonyl]-indol-1-yl}-N,N-dimethyl-acetamide Amide coupling following the general procedure I:
Amine: 1-Piperidin-4-yl-1,3-dihydro-benzoimidazol-2-one (commercially available)
Acid: 6-Chloro-1-dimethylcarbamoylmethyl-5-methyl-1H-indole-3-carboxylic acid.
ES-MS m/e (%): 494.5 (M+H$^+$).

Example 48

2-{5,6-Dichloro-3-[4-(2-oxo-2,3-dihydro-benzoimidazol-1-yl)-piperidine-1-carbonyl]-indol-1-yl}-N,N-dimethyl-acetamide a) 1-(5,6-Dichloro-1H-indol-3-yl)-2,2,2-trifluoro-ethanone

Using a procedure described in *J. Med. Chem.* 1991, 34, 140, from 0.120 g (0.64 mmol) of 5,6-dichloro-1H-indole were prepared 0.11 g (59%) of the title compound as a white solid.

b) 2-[5,6-Dichloro-3-(2,2,2-trifluoro-acetyl)-indol-1-yl]-N,N-dimethyl-acetamide To a stirred solution of 1-(5,6-dichloro-1H-indol-3-yl)-2,2,2-trifluoro-ethanone (0.11 g) in 3 ml of DMF at 0° C., were added 18 mg (1.05 eq.) of NaH (60% in oil). The mixture was stirred for 30 min. and then 0.04 ml (1.0 eq.) of dimethylamino-acetyl chloride were added. The mixture was stirred an additional hour and then poured onto water and extracted with ethyl acetate. The combined organic phases were dried over $Na_2SO_4$ and concentrated in vacuo to afford 112 mg (78%) the title compound as a white solid.

c) 5,6-Dichloro-1-dimethylcarbamoylmethyl-1H-indole-3-carboxylic acid

Using a similar procedure described in *J. Med. Chem.* 1991, 34, 140, from 0.112 g of 2-[5,6-dichloro-3-(2,2,2-trifluoro-acetyl)-indol-1-yl]-N,N-dimethyl-acetamide were prepared 0.047 g (49%) of the title compound as a white solid d) 2-{5,6-Dichloro-3-[4-(2-oxo-2,3-dihydro-benzoimidazol-1-yl)-piperidine-1-carbonyl]-indol-1-yl}-N,N-dimethyl-acetamide Amide coupling following the general procedure I:
Amine: 1-Piperidin-4-yl-1,3-dihydro-benzoimidazol-2-one (commercially available)
Acid: 5,6-dichloro-1-dimethylcarbamoylmethyl-1H-indole-3-carboxylic acid.
ES-MS m/e (%): 515.3 (M+H$^+$).

The invention claimed is:
1. A compound of formula (I-b):

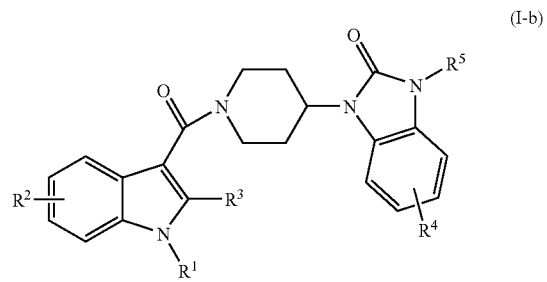

$R^1$ is H,
  $C_{1-6}$-alkyl optionally substituted by CN,
  or is aryl, 5 or 6 membered heteroaryl or sulfonylaryl each of which is optionally substituted by one or more B,
  or is —$(CH_2)_m$—$R^a$ wherein $R^a$ is:
    CN,
    $OR^i$,
    $NR^iR^{ii}$, or
    $C_{3-6}$-cycloalkyl, 4 to 7 membered-heterocycloalkyl, aryl, or 5 or 6 membered heteroaryl each of which is optionally substituted by one or more B,
  or —$(CH_2)_n$—(CO)—$R^b$ or —$(CH_2)_n$—$(SO_2)$—$R^b$, wherein $R^b$ is:
    $C_{1-6}$-alkoxy,
    $C_{3-6}$-cycloalkyl,
    —$(CH_2)_m$—$NR^{iii}R^{iv}$,
    $NR^iR^{ii}$, or
    $C_{3-6}$-cycloalkyl, 4 to 7 membered-heterocycloalkyl, aryl, or 5 or 6 membered heteroaryl each of which is optionally substituted by one or more B,
  or $R^1$ and $R^3$ together with the indole ring to which they are attached form a 5 or 6 membered heterocycloalkyl which is optionally substituted by =O;
there is one or more $R^2$, wherein each $R^2$ is the same or different,
$R^2$ is one or more H, OH, halo, CN, nitro, $C_{1-6}$-alkyl optionally substituted by —$NR^{iii}R^{iv}$, $C_{1-6}$-alkoxy, —O—$CH_2$—$C_{2-6}$-alkenyl, or benzyloxy,
  or two $R^2$ together with the indole ring to which they are attached form an oxo or dioxo bridge;
$R^3$ is H,
  halo,
  —(CO)—$R^c$, wherein $R^c$ is:
    $C_{1-6}$-alkyl,
    —$(CH_2)_n$—$NR^iR^{ii}$,
    —$(CH_2)_n$—$NR^{iii}R^{iv}$ or
    5 or 6 membered heterocycloalkyl optionally substituted by $C_{1-6}$-alkyl, or $C_{1-6}$-alkyl or aryl, each of which is optionally substituted by
    halo,
    —O(CO)—$C_{1-6}$-alkyl, or —NH(CO)R$^d$, wherein R$^d$ is C$_{1-6}$-alkyl optionally substituted by halo or nitro, or R$^d$ is aryl or a 5 or 6 membered heteroaryl, each of which is optionally substituted by halo, nitro, C$_{1-6}$-alkyl or C$_{1-6}$-haloalkyl;

there is one or more R$^4$, wherein each R$^4$ is the same or different,

R$^4$ is one or more H, halo, C$_{1-6}$-alkyl or C$_{1-6}$-alkoxy or two R$^4$ together with the phenyl ring to which they are attached form an oxo or dioxo bridge;

R$^5$ is H, C$_{1-6}$-alkyl, —(CH$_2$)$_m$—NR$^i$R$^{ii}$, aryl, or —(CH$_2$)$_n$—(CO)—R$^b$ wherein R$^b$ is NR$^i$R$^{ii}$ or 4 to 7 membered-heterocycloalkyl, when the dotted line does not represent a double bond, or is absent when the dotted line represents a double bond;

B is halo, CN, NR$^i$R$^{ii}$, C$_{1-6}$-alkyl optionally substituted by CN, halo or C$_{1-6}$-alkoxy, C$_{1-6}$-alkoxy, C$_{1-6}$-haloalkoxy, C$_{3-6}$-cycloalkyl, —C(O)O—C$_{1-6}$-alkyl, —C(O)NR$^i$R$^{ii}$, —C(O)—C$_{1-6}$-alkyl, —S(O)$_2$—C$_{1-6}$-alkyl, —S(O)$_2$—NR$^i$R$^{ii}$, (CR$^{iii}$R$^{iv}$)$_n$-phenyl, or (CR$^{iii}$R$^{iv}$)$_n$-5 or 6 membered heteroaryl wherein the phenyl or 5 or 6 membered heteroaryl moiety is optionally substituted by one or more substituent(s) selected from the group consisting of:

halo, CN, NR$^i$R$^{ii}$, C$_{1-6}$-alkyl optionally substituted by CN or C$_{1-6}$-alkoxy, C$_{1-6}$-alkoxy, C$_{1-6}$-haloalkoxy, C$_{3-6}$-cycloalkyl, —C(O)O—C$_{1-6}$-alkyl, —C(O)—NR$^i$R$^{ii}$, —C(O)—C$_{1-6}$-alkyl, —S(O)$_2$—C$_{1-6}$-alkyl, and —S(O)$_2$—NR$^i$R$^{ii}$;

R$^i$ and R$^{ii}$ are each independently H, C$_{1-6}$-alkyl, C$_{1-6}$-alkyl-NR$^{iii}$R$^{iv}$, —(CO)O—C$_{1-6}$-alkyl, —C(O)—NR$^{iii}$R$^{iv}$, —S(O)$_2$—C$_{1-6}$-alkyl or —S(O)$_2$—NR$^{iii}$R$^{iv}$;

R$^{iii}$ and R$^{iv}$ are each independently H or C$_{1-6}$-alkyl;

m is 1 to 6; and n is 0 to 4;

or a pharmaceutically acceptable salt thereof.

2. The compound of claim 1:

wherein

R$^1$ is H,

C$_{1-6}$-alkyl optionally substituted by CN or by C$_{1-6}$-alkoxy, aryl, 5 or 6 membered heteroaryl, sulfonylaryl, —(CH$_2$)$_m$—R$^a$ wherein R$^a$ is C$_{3-6}$-cycloalkyl, 5 or 6 membered-heterocycloalkyl, aryl, or 5 or 6 membered heteroaryl each of which is optionally substituted by one or more substituents selected from the group consisting of:

halo, CN, C$_{1-6}$-alkyl, C$_{1-6}$-alkoxy, C$_{1-6}$-haloalkoxy, —C(O)O—C$_{1-6}$-alkyl and phenyl optionally substituted by halo, C$_{1-6}$-alkyl, C$_{1-6}$-haloalkyl or C$_{1-6}$-alkoxy, —(CH$_2$)$_m$—NR$^i$R$^{ii}$, or —(CH$_2$)$_n$—(CO)—R$^b$ or —(CH$_2$)$_n$—(SO$_2$)—R$^b$, wherein R$^b$ is:

NR$^i$R$^{ii}$ or 4 to 7 membered-heterocycloalkyl, aryl, or 5 or 6 membered heteroaryl each of which is optionally substituted by one or more halo, C$_{1-6}$-alkyl optionally substituted by CN, halo or C$_{1-6}$-alkoxy, C$_{1-6}$-alkoxy, C$_{1-6}$-haloalkoxy or (CR$^{iii}$R$^{iv}$)$_n$-phenyl;

there is one or more R$^2$, wherein each R$^2$ is the same or different,

R$^2$ is one or more H, halo, CN, nitro, C$_{1-6}$-alkyl, C$_{1-6}$-alkoxy, —O—CH$_2$—C$_{2-6}$-alkenyl, or benzyloxy, or two R$^2$ together with the indole ring to which they are attached form an oxo or dioxo bridge;

R$^3$ is H, halo,

—(CO)—R$^c$, wherein R$^c$ is C$_{1-6}$-alkyl, 5 or 6 membered heterocycloalkyl optionally substituted by C$_{1-6}$-alkyl, or R$^c$ is —(CH$_2$)$_n$—NR$^i$R$^{ii}$, or C$_{1-6}$-alkyl or aryl, each of which is optionally substituted by —O(CO)—C$_{1-6}$-alkyl, or —NH(CO)R$^d$, wherein R$^d$ is C$_{1-6}$-alkyl optionally substituted by halo or nitro, or R$^d$ is aryl or a 5 or 6 membered heteroaryl, each of which is optionally substituted by halo, nitro, C$_{1-6}$-alkyl or C$_{1-6}$-haloalkyl;

there is one or more R$^4$, wherein each R$^4$ is the same or different,

R$^4$ is one or more H, halo, C$_{1-6}$-alkyl or C$_{1-6}$-alkoxy or two R$^4$ together with the phenyl ring to which they are attached form an oxo or dioxo bridge;

R$^5$ is H, C$_{1-6}$-alkyl, —(CH$_2$)$_m$—NR$^i$R$^{ii}$, aryl, or —(CH$_2$)$_n$—(CO)—R$^b$ wherein R$^b$ is NR$^i$R$^{ii}$ or 4 to 7 membered-heterocycloalkyl;

R$^i$ and R$^{ii}$ are each independently selected from H, C$_{1-6}$-alkyl and —(CO)O—C$_{1-6}$-alkyl;

R$^{iii}$ and R$^{iv}$ are H or C$_{1-6}$-alkyl;

m is 1 to 6; and n is 0 to 4;

or a pharmaceutically acceptable salt thereof.

3. The compound of claim 2, wherein:

R$^1$ is H,

C$_{1-6}$-alkyl optionally substituted by CN,

—(CH$_2$)$_m$—R$^a$ wherein R$^a$ is aryl, which is optionally substituted by one or more substituents selected from the group consisting of:

halo, CN, C$_{1-6}$-alkyl, C$_{1-6}$-alkoxy, C$_{1-6}$-haloalkoxy, —C(O)O—C$_{1-6}$-alkyl and phenyl optionally substituted by halo, C$_{1-6}$-alkyl, C$_{1-6}$-haloalkyl or C$_{1-6}$-alkoxy, —(CH$_2$)$_m$—NR$^i$R$^{ii}$, or —(CH$_2$)$_n$—(CO)—R$^b$ or —(CH$_2$)$_n$—(SO$_2$)—R$^b$, wherein R$^b$ is:

NR$^i$R$^{ii}$ or 4 to 7 membered-heterocycloalkyl, aryl, or 5 or 6 membered heteroaryl each of which is optionally substituted by one or more halo, C$_{1-6}$-alkyl optionally substituted by CN, halo or C$_{1-6}$-alkoxy, C$_{1-6}$-alkoxy, C$_{1-6}$-haloalkoxy or (CR$^{iii}$R$^{iv}$)$_n$-phenyl;

there is one or more R$^2$, wherein each R$^2$ is the same or different,

R$^2$ is one or more H, halo or C$_{1-6}$-alkoxy;

R$^3$ is H,

—(CO)—R$^c$, wherein R$^c$ is C$_{1-6}$-alkyl or 5 or 6 membered heterocycloalkyl optionally substituted by C$_{1-6}$-alkyl, or C$_{1-6}$-alkyl;

R$^4$ is H;

R$^5$ is H, —(CH$_2$)$_m$—NR$^i$R$^{ii}$, aryl, or —(CH$_2$)$_n$—(CO)—R$^b$ wherein R$^b$ is NR$^i$R$^{ii}$ or 4 to 7 membered-heterocycloalkyl;

R$^i$ and R$^{ii}$ are each independently selected from H, C$_{1-6}$-alkyl and —(CO)O—C$_{1-6}$-alkyl;

R$^{iii}$ and R$^{iv}$ are each independently H or C$_{1-6}$-alkyl;

m is 1 to 6; and n is 0 to 4;

or a pharmaceutically acceptable salt thereof.

4. The compound of claim 3, selected from the group consisting of:
  1-[1-(1-Benzyl-1H-indole-3-carbonyl)-piperidin-4-yl]-1,3-dihydro-benzoimidazol-2-one;
  1-{1-[(1-benzyl-2-methyl-1H-indol-3-yl)carbonyl]piperidin-4-yl}-3-methyl-1,3-dihydro-2H-benzimidazol-2-one;
  1-[1-(2-Methyl-1H-indole-3-carbonyl)-piperidin-4-yl]-1,3-dihydro-benzoimidazol-2-one;
  1-[1-(1-Isopropyl-6-methoxy-1H-indole-3-carbonyl)-piperidin-4-yl]-1,3-dihydro-benzoimidazol-2-one;
  1-[1-(6-Fluoro-1-isopropyl-1H-indole-3-carbonyl)-piperidin-4-yl]-1,3-dihydro-benzoimidazol-2-one;
  1-[1-(6-Chloro-1-isopropyl-1H-indole-3-carbonyl)-piperidin-4-yl]-1,3-dihydro-benzoimidazol-2-one;
  1-[1-(1-Isopropyl-1H-indole-3-carbonyl)-piperidin-4-yl]-1,3-dihydro-benzoimidazol-2-one;
  1-[1-(1-Methyl-1H-indole-3-carbonyl)-piperidin-4-yl]-1,3-dihydro-benzoimidazol-2-one;
  1-[1-(1H-Indole-3-carbonyl)-piperidin-4-yl]-1,3-dihydro-benzoimidazol-2-one; and
  1-{1-[2-(Pyrrolidine-1-carbonyl)-1H-indole-3-carbonyl]-piperidin-4-yl}-1,3-dihydro-benzoimidazol-2-one.

5. The compound of claim 3, selected from the group consisting of:
  1-[1-(6-Chloro-1H-indole-3-carbonyl)-piperidin-4-yl]-1,3-dihydro-benzoimidazol-2-one;
  1-[1-(6-Chloro-5-fluoro-1H-indole-3-carbonyl)-piperidin-4-yl]-1,3-dihydro-benzoimidazol-2-one;
  1-[1-(1-Benzyl-2-methyl-1H-indole-3-carbonyl)-piperidin-4-yl]-3-(2-dimethylamino-ethyl)-1,3-dihydro-benzoimidazol-2-one;
  {6-Chloro-3-[4-(2-oxo-2,3-dihydro-benzoimidazol-1-yl)-piperidine-1-carbonyl]-indol-1-yl}-acetonitrile;
  1-{1-[2-(2-Methyl-butyryl)-1H-indole-3-carbonyl]-piperidin-4-yl}-1,3-dihydro-benzoimidazol-2-one;
  1-[1-(1-Benzyl-2-methyl-1H-indole-3-carbonyl)-piperidin-4-yl]-1,3-dihydro-benzoimidazol-2-one;
  1-[1-(1-Benzyl-6-chloro-1H-indole-3-carbonyl)-piperidin-4-yl]-1,3-dihydro-benzoimidazol-2-one;
  1-[1-(1-Cyclohexylmethyl-1H-indole-3-carbonyl)-piperidin-4-yl]-1,3-dihydro-benzoimidazol-2-one;
  1-{1-[6-Chloro-1-(2-dimethylamino-ethyl)-1H-indole-3-carbonyl]-piperidin-4-yl}-1,3-dihydro-benzoimidazol-2-one; and
  1-[1-(6-Chloro-1H-indole-3-carbonyl)-piperidin-4-yl]-3-(2-dimethylamino-ethyl)-1,3-dihydro-benzoimidazol-2-one.

6. The compound of claim 3, selected from the group consisting of:
  1-{1-[6-Chloro-1-(3-fluoro-benzoyl)-1H-indole-3-carbonyl]-piperidin-4-yl}-1,3-dihydro-benzoimidazol-2-one;
  1-(1-{6-Chloro-1-[2-(3-fluoro-phenyl)-2-oxo-ethyl]-1H-indole-3-carbonyl}-piperidin-4-yl)-1,3-dihydro-benzoimidazol-2-one;
  1-{1-[6-Chloro-1-(2-fluoro-benzoyl)-1H-indole-3-carbonyl]-piperidin-4-yl}-1,3-dihydro-benzoimidazol-2-one;
  1-{1-[6-Chloro-1-(2,3-difluoro-benzoyl)-1H-indole-3-carbonyl]-piperidin-4-yl}-1,3-dihydro-benzoimidazol-2-one;
  1-{1-[6-Chloro-1-(3,5-difluoro-benzenesulfonyl)-1H-indole-3-carbonyl]-piperidin-4-yl}-1,3-dihydro-benzoimidazol-2-one;
  1-{1-[6-Chloro-1-(3,5-difluoro-benzyl)-1H-indole-3-carbonyl]-piperidin-4-yl}-1,3-dihydro-benzoimidazol-2-one;
  1-{1-[6-Chloro-1-(3-fluoro-benzyl)-1H-indole-3-carbonyl]-piperidin-4-yl}-1,3-dihydro-benzoimidazol-2-one;
  1-(1-{6-Chloro-1-[2-(2,5-difluoro-phenyl)-2-oxo-ethyl]-1H-indole-3-carbonyl}-piperidin-4-yl)-1,3-dihydro-benzoimidazol-2-one;
  1-(1-{6-Chloro-1-[2-(2,4-difluoro-phenyl)-2-oxo-ethyl]-1H-indole-3-carbonyl}-piperidin-4-yl)-1,3-dihydro-benzoimidazol-2-one; and
  1-{1-[6-Chloro-1-(3,5-difluoro-benzoyl)-1H-indole-3-carbonyl]-piperidin-4-yl}-1,3-dihydro-benzoimidazol-2-one.

7. The compound of claim 3, selected from the group consisting of:
  1-(1-{6-Chloro-1-[2-(2-fluoro-phenyl)-2-oxo-ethyl]-1H-indole-3-carbonyl}-piperidin-4-yl)-1,3-dihydro-benzoimidazol-2-one;
  1-(1-{6-Chloro-1-[2-(3,4-difluoro-phenyl)-2-oxo-ethyl]-1H-indole-3-carbonyl}-piperidin-4-yl)-1,3-dihydro-benzoimidazol-2-one;
  1-{1-[6-Chloro-1-(3,5-difluoro-phenyl)-1H-indole-3-carbonyl]-piperidin-4-yl}-1,3-dihydro-benzoimidazol-2-one;
  1-{1-[6-Chloro-1-(piperidine-1-carbonyl)-1H-indole-3-carbonyl]-piperidin-4-yl}-1,3-dihydro-benzoimidazol-2-one;
  1-{1-[6-Chloro-1-(2-oxo-2-piperidin-1-yl-ethyl)-1H-indole-3-carbonyl]-piperidin-4-yl}-3-(2-oxo-2-piperidin-1-yl-ethyl)-1,3-dihydro-benzoimidazol-2-one;
  2-{3-[1-(6-Chloro-1-diethylcarbamoylmethyl-1H-indole-3-carbonyl)-piperidin-4-yl]-2-oxo-2,3-dihydro-benzoimidazol-1-yl}-N,N-diethyl-acetamide;
  1-(1-{6-Chloro-1-[2-(3,5-difluoro-phenyl)-2-oxo-ethyl]-1H-indole-3-carbonyl}-piperidin-4-yl)-1,3-dihydro-benzoimidazol-2-one;
  1-(1-{6-Chloro-1-[2-(5-methyl-2-phenyl-oxazol-4-yl)-2-oxo-ethyl]-1H-indole-3-carbonyl}-piperidin-4-yl)-1,3-dihydro-benzoimidazol-2-one;
  2-{6-Chloro-3-[4-(2-oxo-2,3-dihydro-benzoimidazol-1-yl)-piperidine-1-carbonyl]-indol-1-yl}-N,N-dimethyl-acetamide;
  2-{6-Chloro-5-methyl-3-[4-(2-oxo-2,3-dihydro-benzoimidazol-1-yl)-piperidine-1-carbonyl]-indol-1-yl}-N,N-dimethyl-acetamide; and
  2-{5,6-Dichloro-3-[4-(2-oxo-2,3-dihydro-benzoimidazol-1-yl)-piperidine-1-carbonyl]-indol-1-yl}-N,N-dimethyl-acetamide.

8. A pharmaceutical composition comprising a compound of formula (I-b)

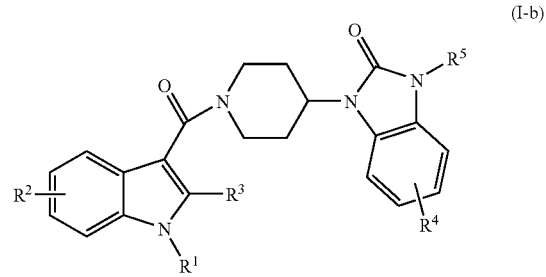

of claim 1 or a pharmaceutically acceptable salt thereof and a pharmaceutically acceptable carrier.

* * * * *